United States Patent [19]
Benko et al.

[11] Patent Number: 5,962,690
[45] Date of Patent: Oct. 5, 1999

[54] BENZOIC ACID COMPOUNDS

[75] Inventors: Zoltan L. Benko; James A. Turner; Gail M. Garvin; Johnny L. Jackson; Sharon L. Shinkle, all of Indianapolis, Ind.

[73] Assignee: Dow AgroSciences LLC, Indianapolis, Ind.

[21] Appl. No.: 09/122,397

[22] Filed: Jul. 24, 1998

Related U.S. Application Data

[62] Division of application No. 09/047,169, Mar. 24, 1998, Pat. No. 5,824,802
[60] Provisional application No. 60/042,351, Mar. 24, 1997.

[51] Int. Cl.⁶ .................... C07D 211/14; C07D 231/12
[52] U.S. Cl. .................. 546/221; 546/235; 548/377.1; 562/430
[58] Field of Search .............. 562/430; 548/377.1; 546/221

[56] References Cited

U.S. PATENT DOCUMENTS

| | | |
|---|---|---|
| Re. 34,408 | 10/1993 | Tanaka et al. . |
| Re. 34,779 | 11/1994 | Oya et al. . |
| 4,063,925 | 12/1977 | Konotsune et al. . |
| 4,146,540 | 3/1979 | Avar et al. . |
| 4,230,481 | 10/1980 | Nishiyama et al. . |
| 4,643,757 | 2/1987 | Baba et al. . |
| 4,744,815 | 5/1988 | Baba et al. . |
| 4,885,022 | 12/1989 | Baba et al. . |
| 4,948,887 | 8/1990 | Baba et al. . |

FOREIGN PATENT DOCUMENTS

| | | |
|---|---|---|
| WO 96/26206 | 8/1996 | WIPO . |
| WO 97/41106 | 11/1997 | WIPO . |

OTHER PUBLICATIONS

Chemical Abstracts, vol. 110(11), abstract No. 95226e, p. 706, published Mar. 13, 1989, which abstracts JP 63 122673 (Nissan Chemical Industries), published May 26, 1988.
Chemical Abstracts, vol. 110(11), abstract No. 95225d, p. 706, published Mar. 13, 1989, which abstracts JP 63 122672 (Nissan Chemical Industries), published May 26, 1988.

*Primary Examiner*—Robert W. Ramsuer
*Attorney, Agent, or Firm*—D. Wendell Osborne

[57] ABSTRACT

1-Alkyl-4-benzoyl-5-hydroxy-1H-pyrazole compounds in which the benzoyl moiety is substituted in the 2-position with groups such as halo or alkyl, in the 4-position with an alkylsulfonyl group, and in the 3-position with an acyclic or cyclic derivatized amino group, such as 1-ethyl-4-(2-chloro-4-methylsulfonyl-3-(morpholin-4-yl)benzoyl-5-hydroxy-1H-pyrazole, were prepared and found to be useful for the control of a variety of broadleaf and grassy weeds. The compounds can be applied either preemergently or postemergently and can be used to control undesirable vegetation in corn, rice, and wheat crops.

6 Claims, No Drawings

BENZOIC ACID COMPOUNDS

CROSS-REFERENCE TO RELATED APPLICATIONS

This application is a Divisional of prior application Ser. No. 09/047,169 filed on Mar. 24, 1998, now U.S. Pat. No. 5,824,802, which claims the benefit of U.S. Provisional Application No. 60/042,351, filed Mar. 24, 1997.

BACKGROUND OF THE INVENTION

This invention relates to novel 1-alkyl-4-benzoyl-5-hydroxypyrazole compounds and to the use of these compounds as herbicides.

A number of 1-alkyl-4-benzoyl-5-hydroxypyrazole compounds and their herbicidal utility have been disclosed in the art, for example, in U.S. Pat. Nos. 4,230,481, 4,063,925, 4,643,757, 4,744,815, 4,885,022, 4,948,881, RE34, 779, RE34,408, and RE34,423. Compounds of this type having a 5- or 6-membered heterocyclic ring substituent attached by means of a carbon—carbon bond to the 3-position of the benzoyl ring were disclosed in PCT Application WO 96/26206, published Aug. 29, 1996.

None of the presently known 1-alkyl-4-benzoyl-5-hydroxypyrazole compounds, however, possess sufficient herbicidal activity coupled with sufficient crop selectivity and desirable toxicological and environmental properties to achieve broad commercial acceptance. It would be highly desirable to discover related compounds that are more potent, more selective, or broader spectrum in their herbicidal activity and/or that have improved toxicological or environmental properties.

SUMMARY OF THE INVENTION

It has now been found that 1-alkyl-4-benzoyl-5-hydroxypyrazole compounds possessing a derivatized amino substituent in the 3-position and selected substituents in the 2- and 4-positions of the benzoyl moiety are potent herbicides with a broad spectrum of weed control and excellent crop selectivity. The compounds, further, possess excellent toxicological and environmental profiles.

The invention includes benzoylpyrazole compounds of Formula I:

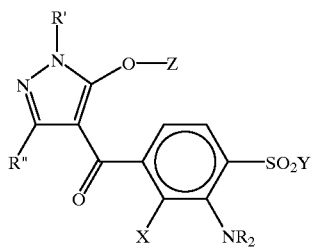

wherein
- X represents F, Cl, Br, $C_1$–$C_4$ alkyl, $OCH_3$, $OC_2H_5$, $Ch_2OCH_3$, or $CH(CH_3)OCH_3$;
- Y represents $CH_3$, $C_2H_5$, or $CH(CH_3)_2$;
- Z represents H or benzyl (optionally possessing up to three ring substituents selected from F, Cl, Br, CN, $CF_3$, $NO_2$, $CH_3$, $C_2H_5$, $OCH_3$, and $OC_2H_5$);
- R' represents $C_1$–$C_4$ alkyl, $C_3$–$C_4$ alkenyl, or $C_3$–$C_4$ alkynyl;
- R" represents H, $Ch_2OCH_3$, or $C_1$–$C_3$ alkyl; and
- each R independently represents H or $C_1$–$C_4$ alkyl, $C_3$–$C_4$ alkenyl, or $C_3$–$C_4$ alkynyl (each optionally possessing up to two substituents selected from Cl, Br, CN, $C_1$–$C_4$ alkoxy, and $C_1$–$C_3$ fluoroalkoxy and up to three F substituents) or benzyl (optionally possessing up to three ring substituents selected from F, Cl, Br, CN, $CF_3$, $NO_2$, $CH_3$, $C_2H_5$, $OCH_3$, and $OC_2H_5$); with the proviso that both of R do not represent H; or
- $NR_2$ represents a 4- to 7-membered aliphatic nitrogen heterocyclic substituent optionally possessing O as a second ring heteroatom, optionally possessing one double bond, and optionally possessing up to three substituents selected from F, Cl, Br, CN, $C_1$–$C_4$ alkyl, $C_1$–$C_3$ fluoroalkyl, $C_1$–$C_4$ alkoxy, $C_1$–$C_3$ fluoroalkoxy, $C_1$–$C_3$ alkoxymethyl, and phenyl (optionally possessing up to three ring substituents selected from F, Cl, Br, CN, $CF_3$, $NO_2$, $CH_3$, $C_2H_5$, $OCH_3$, and $OC_2H_5$); or
- $NR_2$ represents a pyrrol-1-yl or pyrazol-1-yl moiety optionally possessing up to two substituents selected from F, Cl, Br, I, CN, $CF_3$, $C_1$–$C_3$ alkyl, and $C_1$–$C_3$ alkoxy;

and when Z represents H, the agriculturally acceptable salts and esters thereof.

The invention includes herbicidal compositions containing the benzoylpyrazole compounds of Formula I in combination with an agriculturally acceptable adjuvant or carrier as well as a method of use of the compounds to kill or control undesirable vegetation by application of an herbicidal amount of the compound to the vegetation or to the locus of the vegetation. The use of the compounds to kill or control grassy weeds in corn, wheat, barley, and rice is a preferred utility and postemergence application of the compounds to the undesirable vegetation is a preferred method of application.

The invention further includes intermediates useful in preparing the herbicidal benzoylpyrazole compounds of Formula I.

DETAILED DESCRIPTION OF THE INVENTION

The herbicidal compounds of the present invention are benzoylpyrazole compounds of Formula I:

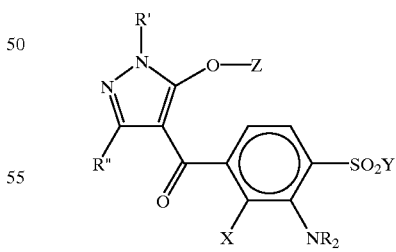

These compounds are characterized by possessing a pyrazole heterocycle moiety substituted in the 1-position with an alkyl group and in the 5-position with an hydroxy or benzyloxy group as well as in the 4-position with a benzoyl moiety. Substitution in the 3-position with a lower alkyl moiety is optional. The benzoyl moiety is characterized by being substituted in the 3-position with a derivatized amino substituent, in the 4-position with a lower alkylsulfonyl substituent, and in the 2-position with a halo, lower alkyl, or lower alkoxy substituent. The compounds include salt and ester compounds obtained by derivatization of the 5-position hydroxy group of the pyrazole moiety. The basic compounds are sometimes named as (2,3,4-trisubstituted phenyl)(1-alkyl-5-hydroxy-1H-pyrazol-4-yl)methanone compounds, but are more often referred to in the art as 1-alkyl-4-(2,3, 4-trisubstituted benzoyl)-5-hydroxy-1H-pyrazolo compounds. The latter terminology is used herein. The compounds of Formula I wherein Z represents hydrogen are, further, sometimes referred to as 1-alkyl-4-(2,3,4-trisubstituted benzoyl)-1H-pyrazolin-5-one compounds; that is, as the keto tautomers of the formula illustrated.

The invention includes compounds of Formula I wherein the pyrazole moiety is substituted in the 1-position (R') with an aliphatic hydrocarbyl group of 1 to 4 carbon atoms including compounds wherein R' represents a $C_1$–$C_4$ alkyl, $C_3$–$C_4$ alkenyl, or $C_3$–$C_4$ alkynyl group. Compounds wherein R' represents methyl, ethyl, 1-methylethyl, 1,1-dimethylethyl, and cyclo-propyl are typically preferred. Those wherein R' represents ethyl, 1-methylethyl, and 1,1-dimethylethyl are typically more preferred.

Compounds of Formula I that are unsubstituted in the 3-position of the pyrazole moiety (R" represents hydrogen) or are substituted at that position with methyl, ethyl, propyl, 1-methylethyl, cyclo-propyl, or methoxymethyl are included in the invention. Generally, compounds wherein R" represents hydrogen are preferred. Compounds wherein R' represents methyl, ethyl, 1-methylethyl, 1,1-dimethylethyl, or cyclo-propyl and R" represents hydrogen are often more preferred.

The compounds of Formula I wherein Z represents hydrogen (5-hydroxy compounds) are believed to be the compounds that actually kill or control undesirable vegetation and are typically preferred. Analogs of such compounds that contain a derivatized hydroxy moiety that is transformed within plants or the environment to a hydroxy group possess essentially the same herbicidal effect and are within the scope of the invention. Specifically identified derivatives within this definition include benzyl ethers (Z represents benzyl which may be substituted with one, two, or three compatible substituents). Suitable benzyl substituents include fluoro, chloro, bromo, cyano, trifluoromethyl, nitro, methyl, ethyl, methoxy, and ethoxy. Benzyl without substituents is typically preferred. The agriculturally acceptable salts obtainable by treating a 5-hydroxy compound of Formula I with a metal hydroxide, a metal carbonate, an amine or an aminium hydroxide compound and esters obtainable by treating a 5-hydroxy compound of Formula I with an acid chloride, such as an alkanoyl chloride, a benzoyl chloride, or an alkylsulfonyl chloride, are also convertible to the hydroxy compound and are included in the invention. Amine salts are often preferred forms of the compounds of Formula I because they are water soluble and lend themselves to the preparation of desirable aqueous based herbicidal compositions.

The invention includes compounds of Formula I wherein the benzoyl moiety is substituted in the 4-position ($SO_2Y$) with a methylsulfonyl, ethylsulfonyl, or 1-methylethylsulfonyl group. Methylsulfonyl groups (Y represents methyl) are typically preferred.

Compounds of Formula I substituted in the 2-position of the benzoyl moiety (X) with a fluoro, chloro, bromo, methoxy, ethoxy, methoxymethyl, 1-methoxyethyl, or a 1 to 4 carbon alkyl group are included in the invention. Compounds wherein X represents chloro or methyl are generally preferred. Compounds wherein X represents chloro or methyl and Y represents methyl are often of special interest.

The derivatized amino substituents present in the 3-position of the benzoyl moiety ($R_2N$) are the most distinguishing characteristic of the compounds of the present invention. Derivatized amino substituents can be described as substituents consisting of a trivalent nitrogen atom, one bond of which is attached to the benzoyl ring, the second of which is attached to an optionally substituted aliphatic hydrocarbyl or benzyl moiety, and the third of which is attached to a hydrogen atom or to an optionally substituted aliphatic hydrocarbyl or benzyl moiety. When two optionally substituted aliphatic hydrocarbyl moieties are present, these moieties and the trivalent nitrogen atom may be joined to create an optionally substituted four to seven membered aliphatic heterocyclic moiety or a five membered aromatic heterocylic moiety.

The derivatized amino substituents of the compounds of the present invention include those wherein one or both of the R groups of the $R_2N$ moiety independently represent $C_1$–$C_4$ alkyl, $C_3$–$C_4$ alkenyl, or $C_3$–$C_4$ alkynyl, each of which may have one or two chloro, bromo, cyano, $C_1$–$C_4$ alkoxy, or $C_1$–$C_3$ fluoroalkoxy substituents and may also have up to three fluoro substituents. It further includes compounds wherein one or both of the R groups are benzyl having up to three ring substituents selected from fluoro, chloro, bromo, cyano, trifluoromethyl, nitro, methyl, ethyl, methoxy, and ethoxy. One of the R groups may be hydrogen. Compounds wherein both of R represent optionally substituted hydrocarbyl or benzyl groups are sometimes preferred. Such compounds wherein both R groups are selected from methyl, ethyl, and 2-methoxyethyl are often more preferred. Compounds wherein one of R represents hydrogen and the other represents methyl, ethyl, or 2-methoxyethyl are also sometimes preferred.

The definition of $NR_2$ further includes compounds wherein this substituent represents a 4-, 5-, 6-, or 7-membered aliphatic nitrogen heterocyclic moiety. These heterocyclic moiety substituents may contain one ring oxygen atom and/or one ring carbon-carbon double bond. They, further, may have one, two, or three substituents selected from fluoro, chloro, bromo, cyano, $C_1$–$C_4$ alkyl, $C_1$–$C_3$ fluoroalkyl, $C_1$–$C_3$ alkoxymethyl, $C_1$–$C_4$ alkoxy, $C_1$–$C_3$ fluoroalkoxy, and phenyl, the phenyl optionally having up to three substituents selected from fluoro, chloro, bromo, cyano, trifluoromethyl, nitro, methyl, ethyl, methoxy, and ethoxy. Such compounds wherein $NR_2$ represents a morpholin-4-yl, piperidin-1-yl, or pyrrolidin-1-yl moiety, each optionally substituted with one or two methyl or methoxy groups, are often preferred. Compounds wherein $NR_2$ represents morpholin-4-yl are especially preferred. The aliphatic heterocyclic $NR_2$ substituents of this type are necessarily attached to the benzoyl moiety by means of a carbon-nitrogen bond.

The term $NR_2$ further includes pyrrol-1-yl and pyrazol-1-yl moieties, which are 5-membered aromatic heterocyclic moieties having one or two nitrogen atoms. Such moieties may have one or two substituents selected from fluoro, chloro, bromo, iodo, cyano, $C_1$–$C_3$ alkyl, $C_1$–$C_3$ alkoxy and trifluoromethyl. Pyrazol-1-yl moieties are generally preferred. The aromatic heterocyclic $NR_2$ substituents of this type are necessarily attached to the benzoyl moiety by means of a carbon-nitrogen bond.

Compounds of Formula I wherein R' represents methyl, ethyl, 1-methylethyl, or 1,1-dimethylethyl; R" represents hydrogen; X represents chloro or methyl; Y represents methyl; and wherein both of R represent one of methyl, ethyl, and 2-methoxyethyl, one of R represents hydrogen and the other represents methyl, ethyl, or 2-methoxyethyl, or $NR_2$ represents morpholin-4-yl, piperidin-1-yl, or pyrrolidin-1-yl (each optionally having one or two methyl or methoxy substituents) are often more preferred. Such compounds wherein $NR_2$ represents morpholin-4-yl are often most preferred.

The herbicidal compounds of the invention are exemplified by the compounds given in Table 1. The nuclear magnetic resonance spectra of some of these compounds are given in Table 1A.

TABLE 1

BENZOYLPYRAZOLE COMPOUNDS

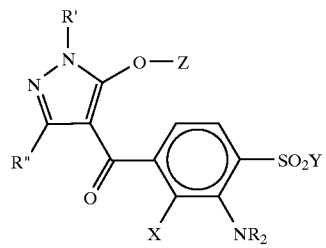

| Cpd. No. | R' | R" | Z | X | Y | $NR_2$ | Form | Melting Point, °C. | Elem. Anal. Calc./Found % C | % H | % N |
|---|---|---|---|---|---|---|---|---|---|---|---|
| 1 | $CH_2CH_3$ | H | H | Cl | $CH_3$ | $N(CH_3)_2$ | off-white solid | 227–228 dec | 48.5 48.7 | 4.88 5.08 | 11.3 11.4 |
| 2 | $CH_2CH_3$ | H | H | Cl | $CH_3$ | $NHCH_3$ | yellow solid | 189–190 | 47.2 47.1 | 4.25 4.55 | 11.8 11.6 |
| 3 | $CH_2CH_3$ | H | H | $CH_3$ | $CH_3$ | $N(CH_3)_2$ | light yellow | 205–206 | 54.7 55.1 | 6.02 6.16 | 12.0 11.6 |
| 4 | $CH_3$ | H | H | Cl | $CH_3$ | $N(CH_3)_2$ | yellow powder | 257–260 | | | |
| 5 | $CH_2CH_3$ | H | H | $CH_3$ | $CH_3$ | $NHCH_3$ | dk yellow crystals | 178–179 | 53.4 53.5 | 5.68 6.02 | 12.5 12.1 |
| 6 | $CH_2CH_3$ | H | H | Cl | $CH_3$ | $NHCH_2C_6H_5$ | tan powder | 107–108 | | | |
| 7 | $CH_3$ | H | H | Cl | $CH_3$ | $NHCH_3$ | yellow powder | 214–216 | | | |
| 8 | $CH(CH_3)_2$ | H | H | Cl | $CH_3$ | $N(CH_3)_2$ | white powder | 186-187 | 49.8 49.6 | 5.22 4.55 | 10.9 10.9 |
| 9 | $CH_2CH_3$ | H | H | $CH_3$ | $CH_3$ | N—$CH_3$ \| $CH_2CH_2OCH_3$ | white powder | 138–139 | 54.7 54.3 | 6.37 6.38 | 10.6 10.3 |
| 10 | $CH_2CH_3$ | H | H | $CH_3$ | $CH_3$ | $NHCH_2CH_2OCH_3$ | lt tan powder | 106–108 | | | |
| 11 | $CH_2CH_3$ | H | H | Cl | $CH_3$ | $NHCH_2CH_2OCH_3$ | white solid | 169–170 | 47.8 48.0 | 5.02 4.76 | 10.6 10.6 |
| 12 | $CH_2CH_3$ | H | H | $CH_3$ | $CH_3$ | $NHCH(CH_3)_2$ | white powder | 99–100 | 55.9 55.7 | 6.34 6.52 | 11.5 11.5 |
| 13 | $CH_2CH_3$ | H | H | Cl | $CH_3$ | N—$CH_3$ \| $CH_2CH_2OCH_3$ | .$H_2O$ orange glass | | 47.1 47.2 | 5.58 5.29 | 9.68 9.42 |
| 14 | $CH(CH_3)_2$ | H | H | $CH_3$ | $CH_3$ | $N(CH_3)_2$ | yellow solid | 175–178 | 55.9 55.8 | 6.34 6.29 | 11.5 11.4 |
| 15 | $CH_2CH_3$ | H | H | $CH_3$ | $CH_3$ | $NHCH_2CH_3$ | yellow powder | 121–123 | | | |
| 16 | $CH_2CH_3$ | H | H | $OCH_3$ | $CH_3$ | $N(CH_3)_2$ | white powder | 214–215 | 52.3 52.4 | 5.76 5.80 | 11.4 11.3 |
| 17 | $CH_2CH_3$ | H | $CH_2C_6H_5$ | $OCH_3$ | $CH_3$ | $N(CH_3)_2$ | white crystals | 125–126 | 60.4 60.2 | 5.95 5.95 | 9.18 9.15 |
| 18 | $CH_2CH_3$ | H | H | Cl | $CH_3$ | $NHCH_2CH_2CH_3$ | yellow | 157–159 | 49.8 | 5.22 | 10.9 |

TABLE 1-continued

BENZOYLPYRAZOLE COMPOUNDS

| Cpd. No. | R' | R" | Z | X | Y | NR₂ | Form | Melting Point, °C. | % C | % H | % N |
|---|---|---|---|---|---|---|---|---|---|---|---|
| 19 | CH₂CH₃ | H | H | CH₃ | CH₃ | NHCH₂CH=CH₂ | powder .½ H₂O lt. tan powder | 102–104 | 49.6 54.9 55.3 | 5.27 5.83 5.47 | 10.6 11.3 11.2 |
| 20 | CH₂CH₃ | H | H | Cl | CH₃ | NHCH₂CH₃ | tan solid | 129–131 | 48.5 48.5 | 4.85 4.87 | 11.3 11.2 |
| 21 | CH₂CH₃ | H | H | Cl | CH₃ | NHCH₂CH₂—OCH₂CH₃ | yellow powder | 134–135 | 49.1 49.3 | 5.33 5.32 | 10.1 10.1 |
| 22 | CH₂CH₃ | H | H | Cl | CH₃ | N(CH₂CH₃)₂ | tan powder | 150–153 | | | |
| 23 | CH₂CH₃ | H | H | Cl | CH₃ | morpholino | white powder | 249–251 | 49.3 48.9 | 4.87 4.83 | 10.2 10.0 |
| 24 | CH₂CH₃ | H | H | Cl | CH₃ | NHCH₂CH=CH₂ | dk yellow solid | 143–144 | 50.5 50.3 | 4.70 4.54 | 11.0 10.9 |
| 25 | CH₂CH₃ | H | H | CH₃ | CH₃ | NHCH₂CF₃ | tan solid | 238–240 | | | |
| 26 | CH₂CH₃ | H | H | F | CH₃ | N(CH₃)₂ | yellow crystals | 175–176 | | | |
| 27 | CH₂CH₃ | H | H | Cl | CH₂CH₃ | N(CH₃)₂ | gold solid | 169–171 | 49.9 49.5 | 5.19 5.37 | 10.9 10.6 |
| 28 | CH₂CH₃ | H | H | CH₂CH₃ | CH₃ | NHCH₃ | yellow powder | 150–152 | 54.7 54.4 | 6.02 5.97 | 12.0 11.9 |
| 29 | CH₂CH₃ | H | H | CH₂CH₃ | CH₃ | N(CH₃)₂ | yellow powder | 177–179 | 55.9 55.6 | 6.34 6.55 | 11.5 11.4 |
| 30 | CH₂CH₃ | H | H | CH₃ | CH₃ | morpholino | lt yellow solid | 216–218 | 55.0 55.3 | 5.85 6.13 | 10.7 10.1 |
| 31 | CH₂CH₃ | H | H | CH₃ | CH₃ | NH-cyclo-C₃H₅ | dk yellow solid | 115–121 | 56.2 56.2 | 5.82 6.00 | 11.6 11.6 |
| 32 | CH(CH₃)₂ | H | H | Cl | CH₃ | morpholino | lt yellow solid | 256–258 | 50.6 50.8 | 5.15 5.29 | 9.85 9.77 |
| 33 | C(CH₃)₃ | H | H | Cl | CH₃ | morpholino | off white solid | 244–246 | 51.7 51.6 | 5.44 5.41 | 9.52 9.40 |
| 34 | CH(CH₃)₂ | H | H | CH₃ | CH₃ | morpholino | lt yellow solid | 210–212 | 56.0 56.0 | 6.18 6.15 | 10.3 10.2 |

TABLE 1-continued

BENZOYLPYRAZOLE COMPOUNDS

| Cpd. No. | R' | R" | Z | X | Y | NR2 | Form | Melting Point, ° C. | Elem. Anal. Calc./Found % C | % H | % N |
|---|---|---|---|---|---|---|---|---|---|---|---|
| 35 | CH(CH3)2 | H | H | CH3 | CH3 |  | off-white solid | 236–239 | 57.0 56.9 | 6.46 6.47 | 9.97 9.72 |
| 36 | CH2CH3 | H | H | Cl | CH3 | 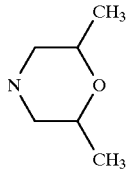 | off-white powder | 207–208 | | | |
| 37 | CH2CH3 | H | H | Cl | CH3 |  | off-white foamy solid | | 51.6 51.5 | 5.47 5.45 | 9.51 9.48 |
| 38 | CH2CH3 | H | H | F | CH3 |  | light tan powder | | | | |
| 39 | CH(CH3)2 | H | H | Cl | CH3 | NHCH2CH2OCH3 | yellow crystals | 155–157 | 49.1 48.9 | 5.33 5.79 | 10.1 9.85 |
| 40 | CH2CH3 | H | H | CH3 | CH3 |  | tan crystal | 149–151 | 57.3 56.9 | 6.14 6.36 | 11.1 11.1 |
| 41 | CH(CH3)2 | H | H | CH3 | CH3 |  | dk brown solid | 196–198 | | | |
| 42 | C(CH3)3 | H | H | CH3 | CH3 |  | black solid | 204–206 | | | |
| 43 | CH2CH3 | H | H | Cl | CH3 |  | yellow crystals | 205–207 | 51.3 51.2 | 5.07 5.04 | 10.6 10.4 |

TABLE 1-continued

BENZOYLPYRAZOLE COMPOUNDS

| Cpd. No. | R' | R" | Z | X | Y | NR₂ | Form | Melting Point, °C. | % C | % H | % N |
|---|---|---|---|---|---|---|---|---|---|---|---|
| 44 | $CH_2CH_3$ | H | H | Cl | $CH_3$ | 3-methylpiperidinyl | dark yellow solid | 203–206 | 53.6 / 53.4 | 5.68 / 6.36 | 9.87 / 9.93 |
| 45 | $CH_2CH_3$ | H | H | Cl | $CH_3$ | 4-methylpiperidinyl | white crystals | 210–213 | 53.6 / 53.2 | 5.68 / 6.07 | 9.87 / 9.80 |
| 46 | $CH(CH_3)_2$ | H | H | Cl | $CH_3$ | piperidinyl | yellow powder | 213–215 | 53.6 / 53.5 | 5.68 / 5.98 | 9.89 / 9.98 |
| 47 | $C(CH_3)_3$ | H | H | Cl | $CH_3$ | piperidinyl | white powder | 247–249 | 54.6 / 54.7 | 5.96 / 6.27 | 9.55 / 9.65 |
| 48 | $C(CH_3)_3$ | H | H | Cl | $CH_3$ | pyrrolidinyl | lt. yellow powder | 216–218 | 53.6 / 53.3 | 5.68 / 5.74 | 9.87 / 10.0 |
| 49 | $CH_2CH_3$ | H | H | $CH_3$ | $CH_3$ | piperidinyl | pale tan solid | 171–173 | 58.3 / 58.3 | 6.44 / 6.89 | 10.7 / 10.8 |
| 50 | $CH(CH_3)_2$ | H | H | Cl | $CH_3$ | pyrrolidinyl | yellow crystals | 217–220 | 52.6 / 52.4 | 5.35 / 5.76 | 10.2 / 10.2 |
| 51 | $CH_2CH_3$ | H | H | Cl | $CH_3$ | $NH(CH_2)_3OCH_3$ | lt yellow powder | 142–143 | 49.1 / 48.9 | 5.33 / 5.26 | 10.1 / 9.89 |
| 52 | $CH_2CH_3$ | H | H | Cl | $CH_3$ | hexamethyleneiminyl | white solid | 230–233 | 53.6 / 53.3 | 5.65 / 5.49 | 9.88 / 9.83 |

TABLE 1-continued

BENZOYLPYRAZOLE COMPOUNDS

| Cpd. No. | R' | R" | Z | X | Y | NR₂ | Form | Melting Point, °C. | Elem. Anal. Calc./Found %C | %H | %N |
|---|---|---|---|---|---|---|---|---|---|---|---|
| 53 | CH₂CH₃ | H | H | Cl | CH₃ | 1,2,3,6-tetrahydropyridine | yellow solid | 178–182 | | | |
| 54 | CH₂CH₃ | H | H | Cl | CH₃ | morpholine | light tan crystals | | | | |
| 55 | CH₂CH₃ | H | H | Cl | CH₃ | 3,3-dimethylpiperidine | tan powder | 191–192 | | | |
| 56 | CH₂CH₃ | H | H | Cl | CH₃ | 3,5-dimethylpiperidine | light tan solid | 202–204 | | | |
| 57 | CH₂CH₃ | H | H | Cl | CH₃ | 4-methoxypiperidine | solid | 138–142 | 51.5 / 51.5 | 5.44 / 5.48 | 9.52 / 9.49 |
| 58 | CH₂CH₃ | H | H | Cl | CH₃ | pyrrole | lt. brown powder | 212–214 | | | |
| 59 | CH₂CH₃ | H | H | Cl | CH₃ | 2-methoxymorpholine | foamy yellow solid | | 48.8 / 49.0 | 5.00 / 5.38 | 9.48 / 8.88 |

TABLE 1-continued

BENZOYLPYRAZOLE COMPOUNDS

| Cpd. No. | R' | R" | Z | X | Y | NR₂ | Form | Melting Point, °C. | % C | % H | % N |
|---|---|---|---|---|---|---|---|---|---|---|---|
| 60 | CH(CH₃)₂ | H | H | Cl | CH₃ | 3-methylpiperidinyl | yellow solid | 224–225 | 54.6 / 54.6 | 5.96 / 5.91 | 9.55 / 9.62 |
| 61 | CH₃ | H | H | Cl | CH₃ | 3-methylpiperidinyl | dark yellow solid | 245–248 | 55.6 / 55.3 | 6.18 / 5.98 | 9.27 / 9.14 |
| 62 | C(CH₃)₃ | H | H | Cl | CH₃ | 3-methylpiperidinyl | off-white solid | 235–238 | 52.6 / 52.4 | 5.35 / 5.47 | 10.2 / 9.79 |
| 63 | CH₂CH₃ | H | H | Cl | CH₃ | 3-methoxypiperidinyl | light yellow crystals | 163–166 | 51.6 / 51.5 | 5.47 / 5.31 | 9.51 / 9.36 |
| 64 | CH₂CH₃ | H | H | Cl | CH₃ | 2-(t-butoxy)morpholinyl | tan solid | 160–163 | 51.9 / 51.9 | 5.81 / 5.71 | 8.65 / 8.55 |
| 65 | CH₂CH₃ | H | H | Cl | CH₃ | pyrazolyl | shiny yellow flakes | 197–198 | 48.7 / 48.5 | 3.83 / 3.76 | 14.2 / 14.0 |
| 66 | CH₂CH₃ | H | H | CH₃ | CH₃ | 3-methylpiperidinyl | yellow solid | 120–123 | 59.4 / 59.3 | 6.78 / 6.71 | 10.6 / 10.4 |

TABLE 1-continued

BENZOYLPYRAZOLE COMPOUNDS

| Cpd. No. | R' | R" | Z | X | Y | NR$_2$ | Form | Melting Point, °C. | Elem. Anal. Calc./Found % C | % H | % N |
|---|---|---|---|---|---|---|---|---|---|---|---|
| 67 | CH$_2$CH$_3$ | H | H | Cl | CH$_3$ | (3,5-dimethylpyrazol-1-yl) | off-white powder | 217–218 | 51.1 / 51.0 | 4.53 / 4.46 | 13.3 / 13.0 |
| 68 | CH$_3$ | H | H | Cl | CH$_3$ | (piperidin-1-yl) | white solid | 266–267 | 48.1 / 48.1 | 4.48 / 4.51 | 10.5 / 10.5 |
| 69 | CH$_2$CH$_3$ | H | H | Cl | CH$_3$ | (2-(CH$_3$)$_2$CHO-morpholin-4-yl) | ½ H$_2$O orange foam | | 50.0 / 50.1 | 5.66 / 5.39 | 8.74 / 8.69 |
| 70 | CH$_2$CH$_3$ | H | H | Cl | CH$_3$ | (2-CH$_3$CH$_2$O-morpholin-4-yl) | ½ H$_2$O orange foam | | 48.9 / 49.2 | 5.50 / 5.28 | 9.00 / 8.95 |
| 71 | CH$_2$CH$_3$ | H | H | Cl | CH$_3$ | (3-CH$_3$CH$_2$O-piperidin-1-yl) | ½ H$_2$O yellow foam | | 51.7 / 52.0 | 5.85 / 5.80 | 9.04 / 8.80 |
| 72 | CH$_2$CH$_3$ | H | H | Cl | CH$_3$ | (4-CH$_3$-pyrazol-1-yl) | pale yellow powder | 215–216 | 49.9 / 49.8 | 4.19 / 4.17 | 13.7 / 13.5 |
| 73 | CH$_2$CH$_3$ | H | H | Cl | CH$_3$ | (3-Cl-piperidin-1-yl) | off-white solid | 177–178 | 48.4 / 48.2 | 4.74 / 4.74 | 9.24 / 10.6 |

TABLE 1-continued
BENZOYLPYRAZOLE COMPOUNDS
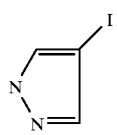
| Cpd. No. | R' | R" | Z | X | Y | NR$_2$ | Form | Melting Point, °C. | Elem. Anal. Calc./Found % C | % H | % N |
|---|---|---|---|---|---|---|---|---|---|---|---|
| 74 | CH$_2$CH$_3$ | H | H | Cl | CH$_3$ | 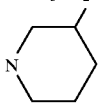 | yellow-tan powder | 218–220 | 36.9 36.8 | 2.71 2.63 | 10.8 10.6 |
| 75 | CH$_2$CH$_3$ | H | H | Cl | CH$_3$ | 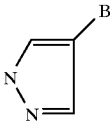 | orange powder | 158–160 | 44.6 44.7 | 4.14 4.15 | 8.21 8.13 |
| 76 | CH$_2$CH$_3$ | H | H | Cl | CH$_3$ | 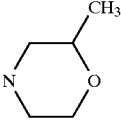 | yellow tan powder | 226–228 | 40.6 40.5 | 2.98 2.89 | 11.8 11.7 |
| 77 | CH$_2$CH$_3$ | H | H | Cl | CH$_3$ | 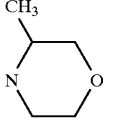 | pale yellow powder | 210–211 | 50.5 50.5 | 5.18 5.21 | 9.82 9.64 |
| 78 | CH$_2$CH$_3$ | H | H | Cl | CH$_3$ | 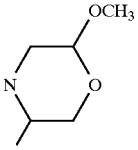 | fluffy pale pink solid | | 50.5 50.1 | 5.18 5.04 | 9.82 9.38 |
| 79 | CH$_2$CH$_3$ | H | H | Cl | CH$_3$ |  | yellow powder | | | | |

TABLE 1-continued

BENZOYLPYRAZOLE COMPOUNDS

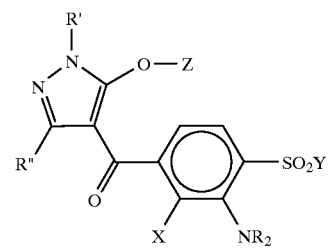

| Cpd. No. | R' | R" | Z | X | Y | NR₂ | Form | Melting Point, °C. | Elem. Anal. Calc./Found % C | % H | % N |
|---|---|---|---|---|---|---|---|---|---|---|---|
| 80 | CH₂CH₃ | H | H | Cl | CH₃ | 2-phenylmorpholinyl | off-white solid | 128-132 dec | 56.4 / 56.3 | 4.94 / 5.01 | 8.58 / 8.31 |
| 81 | CH₂CH₃ | H | H | Cl | CH₃ | 2-phenyl-6-methoxymorpholinyl (trans) | pale pink solid | 169-170 | 55.4 / 55.1 | 5.04 / 5.37 | 8.08 / 7.82 |
| 82 | CH₂CH₃ | H | H | Cl | CH₃ | 2-phenyl-6-methoxymorpholinyl (cis) | pale pink solid | 214-215 | 55.4 / 55.7 | 5.04 / 5.23 | 8.08 / 7.98 |
| 83 | CH₂CH₃ | H | H | Cl | CH₃ | 2-ethylmorpholinyl | orange crystals | 166-167 | 51.6 / 51.7 | 5.47 / 5.57 | 9.51 / 9.46 |
| 84 | CH₂CH₃ | H | H | Cl | CH₃ | 2-ethyl-6-methoxymorpholinyl (cis) | light brown crystals | 160-161 | 50.9 / 51.2 | 5.55 / 5.52 | 8.90 / 8.99 |

TABLE 1-continued

BENZOYLPYRAZOLE COMPOUNDS

| Cpd. No. | R' | R" | Z | X | Y | NR$_2$ | Form | Melting Point, ° C. | Elem. Anal. Calc./Found % C | % H | % N |
|---|---|---|---|---|---|---|---|---|---|---|---|
| 85 | CH$_2$CH$_3$ | H | H | Cl | CH$_3$ | 2-C$_2$H$_5$, 6-OCH$_3$ morpholine (trans) | off-white crystals | 142–143 | 50.9 / 51.1 | 5.55 / 5.52 | 8.90 / 8.94 |
| 86 | CH$_3$ | cyclo-C$_3$H$_5$ | H | Cl | CH$_3$ | morpholine | lt yellow powder | 172–175 | 51.9 / 51.5 | 5.04 / 4.97 | 9.55 / 9.88 |
| 87 | C(CH$_3$)$_3$ | CH$_2$OCH$_3$ | H | Cl | CH$_3$ | morpholine | lt yellow powder | 177–180 | | | |
| 88 | CH$_3$ | CH$_2$CH$_2$CH$_3$ | H | Cl | CH$_3$ | morpholine | lt yellow solid | 215 | | | |
| 89 | CH$_3$ | CH$_3$ | H | Cl | CH$_3$ | morpholine | tan solid | 274 | 49.3 / 49.1 | 4.87 / 4.98 | 10.2 / 9.84 |
| 90 | CH$_2$CH$_2$CH$_3$ | H | H | Cl | CH$_3$ | morpholine | lt yellow solid | 245 | | | |
| 91 | C(CH$_3$)$_3$ | CH$_2$CH$_3$ | H | Cl | CH$_3$ | morpholine | lt yellow powder | 179–181 | | | |
| 92 | C(CH$_3$)$_3$ | CH(CH$_3$)$_2$ | H | Cl | CH$_3$ | morpholine | lt yellow powder | 177–179 | 54.6 / 54.6 | 6.25 / 6.62 | 8.68 / 8.70 |

TABLE 1-continued

BENZOYLPYRAZOLE COMPOUNDS

| Cpd. No. | R' | R" | Z | X | Y | NR_2 | Form | Melting Point, °C. | Elem. Anal. Calc./Found %C | %H | %N |
|---|---|---|---|---|---|---|---|---|---|---|---|
| 93 | CHCH_2CH_3 \| CH_3 | H | H | Cl | CH_3 | morpholino | yellow powder | 261–263 | | | |
| 94 | CH_2CH_3 | H | CH_2C_6H_5 | Cl | CH_3 | piperidino | white glass | | 59.8 59.6 | 5.62 5.65 | 8.37 8.25 |
| 95 | CH_2CH_3 | H | H | Cl | CH_3 | 2-methylpiperidino | yellow powder | 154–157 | 53.6 53.3 | 5.68 5.37 | 9.87 10.1 |
| 96 | cyclo-C_3H_5 | H | H | Cl | CH_3 | morpholino | white powder | 220–221 | 51.6 51.3 | 5.47 6.00 | 9.51 9.37 |

TABLE 1A

SELECTED NMR SPECTRA

| Cpd. No. | 1H NMR(300 MHZ), δ ppm |
|---|---|
| 4 | DMSO-d6: 7.92(d, 1H, J=8.05Hz), 7.48(d, 1H, J=8.05Hz), 7.37(s, 1H), 3.54(s, 3H), 3.40(s, 3H), 2.87(s, 6H). |
| 6 | CDCl_3: 7.87(d, 1H, J=8.04Hz), 7.30(m, 6H), 7.03(d, 1H, J=8.04Hz), 4.63(s, 2H), 4.04(q, 2H, J=7.33Hz), 2.82(s, 3H), 1.43(t, 3H, J=7.14Hz) |
| 7 | DMSO-d6: 7.77(d, 1H, J=8.11Hz), 7.35(s, 1H), 7.01(d, 1H, J=8.11Hz), 3.54(s, 3H), 3.31(s, 3H), 3.06(s, 3H) |
| 8 | CDCl_3: 8.14(d, 1H, J=8.0Hz), 7.52(d, 1H, J=8.0Hz), 7.38(s, 1H), 4.62(hpt, 1H, J=6.7Hz), 3.36(s, 3H), 2.99(s, 6H), 1.53(d, 6H, J=6.7Hz) |
| 9 | CDCl_3: 8.04(d, 1H, J=8.4Hz), 7.40(d, 1H, J=8.4Hz), 7.34(s, 1H), 4.18(q, 2H, 7.2Hz), 3.67(q, 2H, J=5.4Hz), 3.37(s, 3H), 3.34(s, 3H), 3.20–3.50(m, 2H), 2.95(s, 3H), 2.38(s, 3H), 1.46(t, 3H, J=7.2Hz) |
| 10 | CDCl_3: 7.85(d, 1H, J=8.1Hz), 7.37(s, 1H), 7.08(d, 1H, J=8.1Hz), 4.08(q, 2H, J=7.3Hz), 3.62(t, 2H, J=5.0Hz), 3.38–3.44(m, 5H), 3.22(s, 3H), 2.32(s, 3H) 1.46(t, 3H, J=7.3Hz) |
| 13 | CDCl_3: 8.1(d, 1H, J=8.1Hz), 7.4(d, 1H, J=8.1Hz), 7.29(s, 1H), 4.05(q, 2H, J=6.0Hz), 3.6(m, 3H), 3.4(s, 3H), 3.3(s, 3H), 3.22(m, 1H), 2.95(s, 3H), 1.41(t, 3H, J=6.0Hz) |
| 15 | CDCl_3: 7.83(d, 1H, J=7.5Hz), 7.36(s, 1H), 7.06(d, 1H, J=7.5Hz), 4.09(q, 2H, J=8.4Hz), 3.28(q, 2H, J=4.8Hz) 3.1(s, 3H), 2.32(s, 3H), 1.46(t, 3H, J=3.6Hz), 1.31(t, 3H, J=3.6Hz) |
| 22 | CDCl_3: 8.25(d, 1H, J=7.9Hz), 7.42(d, 1H, J=7.9Hz), 7.29(s, 1H), 4.05(q, 2H, J=6.1Hz), 3.4(s, 3H), 3.35(m, 4H), 1.45(t, 3H, J=6.0Hz), 1.22(m, 6H) |
| 25 | CDCl_3: 7.95(d, 1H, J=8Hz), 7.42(s, 1H), 7.28(d, 1H, J=8Hz), 6.20(bt, 1H), 4.10(q, 2H, J=7Hz), 3.90(m, 2H), 3.25(s, 1H), 2.40(s, 1H), 1.50(t, 3H, J=7Hz) |
| 26 | CDCl_3: 7.97(d, 1H, J=7.0Hz), 7.59(dd, 1H, J=6.0 & 8.2Hz), 7.49(s, 1H), 4.08(q, 2H, J=7.2Hz), 3.37(s, 3H), 2.91(s, 6H), 1.46(t, 3H, J=7.2Hz) |
| 30 | CDCl_3: 8.02(d, 1H, J=8Hz), 7.38(d, 1H, J=8Hz), 7.30(s, 1H), 4.02(q, 2H, J=7Hz), 3.80(m, 4H), 3.55(m, 2H), 3.30(s, 3H), 2.95(bd, 2H, J=12Hz), 2.45(s, 3H), 1.42(t, 3H, J=7Hz) |
| 36 | DMSO-d6: 7.95(d, 1H, J=7.9Hz), 7.48(d, 1H, J=7.9Hz), 7.34(bs, 1H), 3.90(q, 2H, J=6.9Hz), 3.45(m & s, 5H), |

TABLE 1A-continued

SELECTED NMR SPECTRA

| Cpd. No. | $^1$H NMR(300 MHZ), δ ppm |
|---|---|
|  | 2.98(bd, 2H, J=11Hz), 1.70(m, 4H), 1.25(t, 3H, J=6.9Hz) |
| 37 | CDCl$_3$: 8.15(d, 1H, J=8.0Hz), 7.44(d, 1H, J=8.0Hz), 7.30(s, 1H), 4.08(q, 2H, J=7.2Hz), 3.90(m, 2H), 3.40(m, 2H), 3.37(s, 3H), 2.80(m, 2H), 1.46(t, 3H, J=7.2Hz), 1.21(d, 6H, J=6.3Hz) |
| 39 | CDCl$_3$: 7.90(d, 1H, J=8Hz), 7.35(s, 1H), 7.00(d, 1H, J=8Hz), 4.60(m, 1H), 3.75(m, 2H), 3.60(m, 2H), 3.40(s, 3H), 3.25(s, 3H), 1.50(d, 6H, J=6Hz) |
| 41 | CDCl$_3$: 8.05(d, 1H, J=8Hz), 7.45(d, 1H, J=8Hz), 7.35(s, 1H), 4.60(m, 1H), 3.30(m, 4H), 3.25(s, 3H), 2.32(s, 3H), 2.05(d, 6H, J=6Hz), 1.50(d, 6H, J=6Hz) |
| 42 | CDCl$_3$: 8.05(d, 1H, J=8Hz), 7.40(d, 1H, J=8Hz), 7.30(s, 1H), 3.30(m, 4H), 3.25(s, 3H), 2.30(s, 3H), 2.05(m, 1H), 1.70(s, 9H) |
| 53 | CDCl$_3$: 8.15(d, 1H, J=7Hz), 7.45(d, 1H, J=7Hz), 7.35(s, 1H), 5.90(m, 2H), 4.30(m, 1H), 4.10(q, 2H, J=7Hz), 3.70(m, 1H), 3.35(s, 3H), 3.30(m, 1H), 3.15(m, 1H), 2.70(m, 1H), 2.05(m, 1H), 1.45(t, 3H, J=7Hz) |
| 54 | CDCl$_3$: 8.15(d, 1H, J=8.8Hz), 8.44(d, 1H, J=8.8Hz), 7.30(s, 1H), 5.18(d, 1H, J=10Hz), 4.48(d, 1H, J=10Hz), 4.15(m, 1H), 4.05(q, 2H, J=8.0Hz), 3.60(m, 2H), 3.55(s, 3H), 3.35(m, 1H), 2.35(m, 1H), 1.50(bd, 1H, J=12Hz), 1.45(t, 3H, J=8.0Hz). |
| 55 | CDCl$_3$: 8.10(d, 1H, J=9.3Hz), 7.45(d, 1H, J=9.3Hz), 7.30(s, 1H), 4.05(q, 2H, J=8.0Hz), 3.55(m, 1H), 3.40(m, 1H), 3.32(s, 1H), 2.90(m, 1H), 2.70(bd, 1H, J=10.0Hz), 1.85(m, 1H), 1.60(m, 1H), 1.40(m & t, 4H, J=8.0Hz), 1.25(m, 1H), 1.15(s, 3H), 0.90(s, 3H) |
| 58 | CDCl$_3$: 8.27(d, 1H, J=8.2Hz), 7.68(d, 1H, J=8.2Hz), 7.38(s, 1H), 6.85(t, 2H, J=2.8Hz), 6.43(t, 2H, J=2.8Hz), 4.15(q, 2H, J=7.2Hz), 2.61(s, 1H), 1.44(t, 3H, J=7.2Hz) |
| 59 | CDCl$_3$: 8.13(m, 1H), 7.44(m, 1H), 7.29(bs, 1H), 4.73 & 4.61(bd & dd, 1H, J=2.7, 2.7 & 8.0Hz), 4.25(m, 2H), 4.07(q, 2H, J=8.0Hz), 3.61 & 3.53(s & s, 3H), 3.54(m, 2H), 3.41 & 3.32(s & s, 3H), 3.07(m, 1H), 2.85(m, 1H), 1.45(t, 3H, J=8.0Hz) |
| 69 | CDCl$_3$: 8.15(m, 1H), 7.44(m, 1H), 7.28(bs, 1H), 4.96 & 4.78(bs & dd, J=3.5 & 11Hz), 4.30(m, 2H), 4.04(m, 3H), 3.84(m, 1H), 3.64 & 3.34(s & s, 3H), 3.56(m, 2H), 3.08(m, 1H), 2.80(m, 1H), 1.45(t, 3H, J=7.0Hz), 1.25(m, 3H), 1.14(m, 3H) |
| 70 | CDCl$_3$: 8.12(m, 1H), 7.40(m, 1H), 4.80 & 4.68(bs & dd, 1H, J=3.5 & 11Hz), 4.30–3.40(m, 8H), 3.55 & 3.30(s & s, 1H), 3.05(m, 1H), 2.82(m, 1H), 1.43(t, 3H, J=6.7Hz), 1.22(m, 3H) |
| 71 | CDCl$_3$: 8.05(m, 1H), 7.40(m, 1H), 7.30(bs, 1H), 4.00(m, 2H), 3.60(m, 4H), 3.30(m & s, 1H & 3H), 3.00(m, 1H), 2.10(m, 1H), 1.70(m, 1H), 1.40(t, 3H, J=7.5Hz), 1.30(m, 1H), 1.20(t, 3H, J=7.5Hz) |
| 77 | CDCl$_3$: 8.14(d, 1H, J=8.1Hz) 7.45(d, 1H, J=8.1Hz), 7.30(s, 1H), 4.18(q, 2H, J=7.2Hz), 3.80–4.00(m, 4H), 3.50(t, 1H, J=10.5Hz), 3.38(s, 3H), 2.92(d, 1H, J=8.7Hz) 2.86(d, 1H, J=11.1Hz) 1.46(t, 3H, J=7.2Hz), 1.20(d, 3H, J=6.3Hz) |
| 78 | CDCl$_3$: 8.20(d, 1H, J=8.0Hz), 7.45(d, 1H, J=8.0Hz), 7.42(s, 1H), 4.25(m, 1H), 4.14(q, 2H, J=7.1 & 14.2Hz), 3.92(m, 3H), 3.58(m, 1H), 3.48(s, 1H), 3.45(m, 3H), 3.16(m, 1H), 1.48(t, 3H, J=7.2Hz), 0.87(d, 3H, J=5.8Hz) |
| 87 | CDCl$_3$: 8.1(d, 1H, J=6.0Hz), 7.37(d, 1H, J=6.0Hz), 3.85(m, 8H), 3.37(s, 3H), 2.75(bd, 2H), 2.74(s, 3H), 1.61(s, 9H) |
| 88 | CDCl$_3$: 8.14(d, 1H, J=8.1Hz), 7.35(d, 1H, J=8.1Hz) 3.86(m, 6H), 3.63(s, 3H), 3.36(s, 3H), 2.84(d, 2H, J=8.9Hz), 1.97(t, 2H, J=7.2Hz), 1.27(m, 2H), 0.61(t, 3H, J=7.2Hz) |
| 90 | CDCl$_3$: 8.14(d, 1H J=8.1Hz), 7.40(d, 1H, J=8.1Hz), 7.32(s, 1H), 3.91(m, 8H), 3.10(s, 3H), 2.87(m, 2H, J=10.7Hz), 1.9(m, 2H), 0.97(t, 3H, J=7.5Hz) |
| 91 | CDCl$_3$: 8.15(d, 1H, J=6.0Hz), 7.35(d, 1H, J=6.0Hz), 3.9(m, 6H), 3.39(s, 3H), 2.75(bd, 2H), 2.0(q, 2H, J=6.0Hz), 1.65(s, 9H), 0.9(t, 3H, J=6.0Hz) |

As noted above, the invention includes the agriculturally acceptable salts and esters of compounds of Formula I wherein Z represents hydrogen, which compounds are readily transformable into compounds wherein Z represents hydrogen and which possess essentially identical herbicidal properties. The 5-position hydroxy group of the pyrazole ring of such compounds is weakly acidic and forms both salts and esters readily. Agriculturally acceptable salts and esters are defined as those salts and esters of the 5-position hydroxy group of the pyrazole ring of the compounds of Formula I (wherein Z represents hydrogen) having a cation or acid moiety that is not, itself, significantly herbicidal to any crop being treated and is not significantly deleterious to the applicator, the environment, or the ultimate user of any crop being treated.

Suitable esters include those derived from optionally substituted aliphatic and aromatic carboxylic acids, examples of which are $C_1$–$C_8$ alkylcarboxylic acids, $C_3$–$C_8$ alkenylcarboxylic acids, and benzoic acid. Suitable esters further include alkylsulfonyl esters derived from alkylsulfonic acids. $C_1$–$C_4$ alkanoyl and benzoyl esters are generally preferred.

Suitable cations include, for example, those derived from alkali or alkaline earth metals and those derived from ammonia and amines. Preferred cations include sodium, potassium, magnesium, and aminium cations of the formula:

wherein $R^5$, $R^6$, and $R^7$ each, independently represents hydrogen or $C_1$–$C_{12}$ alkyl, $C_3$–$C_{12}$ cycloalkyl, or $C_3$–$C_{12}$ alkenyl, each of which is optionally substituted by one or more hydroxy, $C_1$–$C_8$ alkoxy, $C_1$–$C_8$ alkylthio or phenyl groups, provided that $R^5$, $R^6$, and $R^7$ are sterically compatible. Additionally, any two of $R^5$, $R^6$, and $R^7$ together may represent an aliphatic difunctional moiety containing 1 to 12 carbon atoms and up to two oxygen or sulfur atoms. Salts of the compounds of Formula I can be prepared by treatment of compounds of Formula I with a metal hydroxide, such as sodium hydroxide, or an amine, such as ammonia, trimethylamine, diethylamine, 2-methylthiopropylamine, bisallylamine, 2-butoxyethylamine, morpholine, cyclododecylamine, or benzylamine.

The terms alkyl, alkenyl, and alkynyl as used herein includes straight chain, branched chain, and cyclic moieties. Thus, typical alkyl groups are methyl, ethyl, 1-methylethyl, propyl, cyclopropyl, cyclopropylmethyl, methylcyclopropyl, and the like. Methyl, ethyl, and 1-methylethyl are often preferred. Typical mono or disubstituted alkyl groups include 2-chloroethyl, methoxymethyl, 2-methoxyethyl, difluoromethyl, methoxycarbonylmethyl, and 2-ethoxy-1-methylethyl. Methoxymethyl and 2-methoxyethyl are preferred such groups in many circumstances. The term fluoroalkyl includes aikyl groups as defined hereinabove wherein one to all of the hydrogen atoms are replaced by fluorine atoms. Examples include trifluoromethyl, mono-fluoromethyl, 3,3,3-trifluoroethyl, 1,2,2-trifluoroethyl and the like; trifluoromethyl is generally a preferred fluoroalkyl group.

Compounds of Formula I can generally be prepared by the reaction of an appropriate amine compound of Formula II:

with a (3-halobenzoyl)pyrazole compound of Formula III:

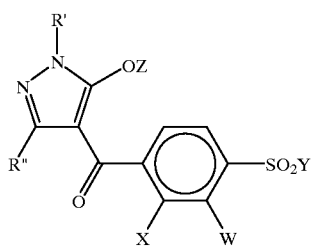

wherein W represents fluoro or chloro and R', R", X, Y, Z, and $NR_2$ have the same definition as they do in the compounds of Formula I. Compounds of Formula III wherein W represents fluoro are superior intermediates because they are more reactive than the corresponding chloro compounds and give better yields under milder conditions. When the amine compound of Formula II is an acyclic aliphatic amine, a benzylamine, or a cyclic aliphatic amine, the reaction is generally carried out using an excess of the amine (more than two moles). Sodium carbonate is also sometimes used as an acid acceptor. Water and/or excess amine are typically used as the solvent, but in some instances a dipolar, aprotic solvent, such as N-methyl-2-pyrrolidinone, or an alcohol can be used as well. The starting material of Formula III and the desired product of Formula I are generally soluble in such media, particularly at higher temperatures, which promotes the reaction. The reaction is generally carried out at temperatures of about 70° C. to about 180° C., preferably at about 80° C. to about 120° C. In the case of low boiling aliphatic amines, such as dimethylamine, a pressure vessel is generally employed. The compounds of Formula I obtained can be recovered by conventional means. Typically, the reaction mixture is acidified with aqueous hydrochloric acid and extracted with dichloromethane. The compounds of Formula I are insufficiently basic to form water-soluble hydrochloride salts under these circumstances whereas the unreacted residual amines are sufficiently basic and are soluble. The dichloromethane solvent and other volatiles can be removed by distillation or evaporation to obtain the desired compound of Formula I as a solid. The compounds of Formula I can be purified by standard procedures, such as by recrystallization or chromatography.

When the amine compound of Formula II is a primary amine, a by-product believed to be the Schiff's base derived from the benzoyl carbonyl group is often obtained in significant amounts. This by-product can be converted to the desired compound of Formula I by heating the reaction mixture with a base in an aqueous alcohol medium before product recovery.

When the (3-halobenzoyl)pyrazole compound of Formula III has a 2-halo substituent on the benzoyl ring; that is, it is a (2,3-dihalobenzoyl)pyrazole compound, a significant side reaction usually occurs wherein the 5-position hydroxy group of the pyrazole moiety reacts with the 2-position halogen of the benzoyl moiety to form a benzopyranone compound of Formula IV:

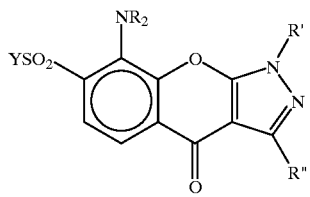

This by-product can be minimized by the use of an aqueous or amine medium, by careful temperature control, and by using a (3-halobenzoyl)pyrazole compound of Formula III wherein W represents fluoro.

Aromatic 5-membered heterocyclic amines, which are not very basic, do not react directly with (3-halobenzoyl) pyrazole compounds of Formula III. Compounds of Formula I wherein $NR_2$ represents an aromatic heterocyclic group can be prepared by treating the amine with a very strong base, such as sodium hydride, and causing the resulting amine anion to react. Typically, about equimolar amounts of the pyrrole or pyrazole compound of Formula II and (3-halobenzoyl)pyrazole compound of Formula III are used along with a small excess of the base. The reaction is typically carried out in a dipolar, aprotic solvent such as N,N-dimethylformamide at about 25° C. to about 50° C. The products obtained can be recovered and purified as described for aliphatic analogs. The use of (3-fluorobenzoyl)pyrazole compounds of Formula III (W represent fluoro) as the starting material generally gives the best results, but the (3-chlorobenzoyl)pyrazole analogs are often used because of their availability and lower cost.

The 3-fluorobenzoylpyrazole compounds of Formula III (compounds of Formula III wherein W represents F) have not been disclosed in the art. These compounds can be prepared from 2-substituted-3-fluoro-4-alkylsulfonylbenzoic acids of Formula V:

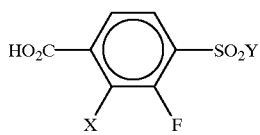

wherein X and Y are as defined for compounds of Formula I by reaction with appropriate 1-alkyl-5-hydroxypyrazole compounds of Formula VI:

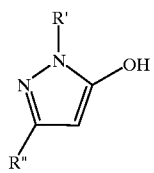

wherein R' and R" are as defined for compounds of Formula I. The auxilliary reagents and reaction conditions described herein for the corresponding preparation of compounds of Formula I from a benzoic acid compound and a 5-hydroxypyrazole compound (vide infra) and other methods well established in the art for the corresponding preparation of related compounds are generally employed. Suitable preparative methods are disclosed, for example, in U.S. Pat. Nos. 4,063,925, 4,885,022, and 4,986,845. The (3-chlorobenzoyl)pyrazole compounds of Formula III can be prepared in the same manner.

2-Substituted-3-fluoro-4-alkylsulfonylbenzoic acid compounds of Formula V can generally be prepared from 1-bromo-2-substituted-3-fluoro-4-alkylthiobenzene compounds by sequential treatment with butyl lithium and carbon dioxide in tetrahydrofuran followed by oxidation with hydrogen peroxide in acetic acid. Alternately, these compounds can be prepared by oxidation of the same starting material with hydrogen peroxide in acetic acid followed by carbonation with carbon monoxide in the presence of a palladium acetate:(diphenylphosphono)butane complex, sodium acetate, and ethanol. 1-Bromo-2-substituted-3-fluoro-4-alkylthiobenzene compounds can be prepared from 1-substituted-2-fluoro-3-alkylthiobenzene compounds by bromination in the presence of ferric chloride. Many 1-substituted-2-fluoro-3-alkylthiobenzene compounds can be prepared by treatment of 1-substituted-2-fluorobenzene compounds sequentially with butyl lithium and a dialkyl disulfide compound in tetrahydrofuran.

The compounds of Formula I can also generally be prepared from an appropriately substituted benzoic acid compound of Formula VII:

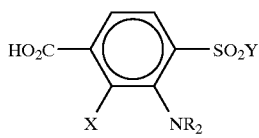

wherein X, Y, and R are as defined for compounds of Formula I and an appropriate 1-alkyl-5-hydroxypyrazole compound of Formula VI:

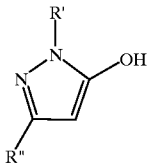

wherein R' and R" are as defined for compounds of Formula I. The coupling can be carried out under reaction conditions known in the art for reactions of other benzoic acid compounds with 1-alkyl-5-hydroxypyrazole compounds to form benzoylpyrazoles. Suitable preparative methods are disclosed, for example, in U.S. Pat. Nos. 4,063,925, 4,885,022, and 4,986,845. One of these methods involves conversion of the benzoic acid compound of Formula VII to its acid chloride with thionyl chloride, coupling this acid chloride with a 5-hydroxypyrazole compound of Formula VI in the presence of triethylamine, and rearranging the originally formed ester and/or amide product with a cyanide ion catalyst, typically supplied by adding acetone cyanohydrin or potassium cyanide. Another method involves the reaction of a benzoic acid compound of Formula VII with a 5-hydroxypyrazole compound of Formula VI in the presence of dicyclohexylcarbodimide and isomerization of the originally formed ester with a cyanide ion catalyst. The compounds of Formula I obtained by these methods can be recovered using the methods known in the art for related compounds.

The 3-(substituted amino)benzoic acid compounds of Formula VII can be prepared by the reaction of an appropriate amine compound of Formula II with an appropriate 3-halobenzoic acid compound. 3-Chloro and 3-fluorobenzoic acid compounds are generally used. The 3-fluoro compounds of Formula V are often preferred because of their higher reactivity. The reaction conditions employed are essentially the same as those used to prepare compounds of Formula I from compounds of Formula III described hereinabove.

Compounds of Formulas I and VII and related compounds prepared by the procedures outlined above can be converted into other compounds of Formulas I and VII by standard procedures known to those in the art.

3-(Hydroxyalkylamino) substituted compounds are useful intermediates for the preparation of compounds of Formulas I and VII having cyclic amino substituents and (alkoxyalkyl) amino substituents. Compounds having 2-hydroxyalkylamino substituents, such as 2-hydroxyethylamino, react with glyoxal to produce compounds having morpholin-2-on-4-yl (2-oxo-tetrahydro-1,4-oxazin-4-yl) substituents. These compounds can be converted by reduction to compounds having 2-hydroxymorpholin-4-yl and morpholin-4-yl substituents, each optionally possessing additional alkyl or phenyl substituents. Compounds having 2-hydroxymorpholin-4-yl substituents can be further converted to compounds having 2-alkoxymorpholin-4-yl substituents with alcohols in the presence of anhydrous hydrogen chloride or boron trifluoride etherate. Compounds having 3-hydroxypropylamino substituents react with formaldehyde to give compounds having tetrahydro-1,3-oxazin-3-yl substituents. When Z represents benzyl, compounds of Formula I having a 3-(hydroxyalkyl)amino (including hydroxy substituted aliphatic heterocyclyl) substituent can be alkylated with alkyl bromides, iodides, or sulfates using standard procedures.

Compounds of Formula I wherein Z represents hydrogen can be converted into corresponding compounds of Formula I wherein Z represents optionally substituted benzyl by treatment with an optionally substituted benzyl chloride or bromide using reaction conditions well-known in the art to promote similar etherification reactions. For example, approximately equimolar amounts of the reactants can be combined in an alcohol or a dipolar, aprotic solvent, a non-reactive base, such as a tertiary amine or an alkali metal carbonate, added, and the mixture heated. Salts of compounds of Formula I wherein Z represents hydrogen can be prepared by treatment with an equimolar amount of an appropriate metal hydroxide, amine, or aminium hydroxide compound. Esters of compounds of Formula I wherein Z represents hydrogen can be made by treatment with equimolar amounts of an appropriate acid chloride compound and a tertiary amine compound, typically in an inert solvent. Reaction conditions known in the art for similar esterification reactions can be used. In each case the compounds prepared can be recovered by standard techniques.

The amine compounds of Formula II are known in the art or can be prepared by methods known in the art.

The compounds of Formula I have been found to be useful preemergence and postemergence herbicides. They can be employed at non-selective (higher) rates of application to control a broad spectrum of the vegetation in an area or, in some cases, at selective (lower) rates of application for the selective control of undesirable vegetation in grass crops, such as corn, wheat, barley, and rice, as well as in broadleaf crops, such as soybeans and cotton. It is usually preferred to employ the compounds postemergence. It is further usually preferred to use the compounds to control a broad spectrum of weeds, including grassy weeds, such as barnyardgrass and giant foxtail, in corn, wheat, or barley crops. While each of the benzoylpyrazole compounds encompassed by Formula I is within the scope of the invention, the degree of herbicidal activity, the crop selectivity, and the spectrum of weed control obtained varies depending upon the substituents present. An appropriate compound for any specific herbicidal utility can be identified by using the information presented herein and routine testing.

The term herbicide is used herein to mean an active ingredient which kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings and established vegetation.

Herbicidal activity is exhibited by the compounds of the present invention when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the compounds of Formula I post-emergence to relatively immature undesirable vegetation to achieve the maximum control.

Application rates of about 1 to about 500 g/Ha are generally employed in postemergence operations; for preemergence applications, rates of about 10 to about 1000 g/Ha are generally employed. The higher rates designated generally give non-selective control of a broad variety of undesirable vegetation. The lower rates typically give selective control and, by judicious election, can be employed in the locus of crops.

The herbicidal compounds of the present invention are often best applied in conjunction with one or more other herbicides to obtain control of a wider variety of undesirable vegetation. When used in conjunction with other herbicides, the presently claimed compounds can be formulated with the other herbicide or herbicides, tank mixed with the other herbicide or herbicides, or applied sequentially with the other herbicide or herbicides. Some of the herbicides that can be employed in conjunction with the compounds of the present invention include sulfonamides such as metosulam, flumetsulam, cloransulam-methyl, diclosulam, and N-2,6-dichlorophenyl-5-ethoxy-7-fluoro[1,2,4]triazolo-[1,5-c]pyrimidine-2-sulfonamide, sulfonylureas such as chlorimuron, nicosulfuron and metsulfuron, imidazolidones such as imazaquin, imazethapyr and imazamox, phenoxyalkanoic acids such as 2,4-D and MCAA, pyridinyloxyacetic acids such as triclopyr and fluroxypyr, carboxylic acids such as clopyralid and dicamba, dinitroanilines such as trifluralin and pendimethalin, chloroacetanilides such as alachlor, acetochlor and metolachlor and other common herbicides including acifluorfen, bentazon, clomazone, fumiclorac, fluometuron, fomesafen, lactofen, linuron, isoproturon, and metribuzin. They can, further, be used in conjunction with glyphosate and glufosinate. It is generally preferred to use the compounds of the invention in combination with herbicides that are selective for the crop being treated and which complement the spectrum of weeds controlled by these compounds at the application rate employed. It is further generally preferred to apply the compounds of the invention and complementary other herbicides at the same time, either as a combination formulation or as a tank mix.

The compounds of the present invention can generally be employed in combination with known herbicide safeners, such as cloquintocet, furilazole, dichlormid, benoxacor, flurazole, and fluxofenim, to enhance their selectivity. They can additionally be employed to control undesirable vegetation in many crops that have been made tolerant to or resistant to them or to other herbicides by genetic manipulation or by mutation and selection. For example, corn, wheat, rice, soybean, sugarbeet, cotton, canola, and other crops that have been made tolerant or resistant to compounds that are hydroxyphenylpyruvate dioxygenase inhibitors in sensitive plants can be treated. Many glyphosate and glufosinate tolerant crops can be treated as well.

While it is possible to utilize the benzoylpyrazole compounds of Formula I directly as herbicides, it is preferable to use them in mixtures containing an herbicidally effective amount of the compound along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with the compounds of Formula I or other composition ingredients. Such mixtures can be designed for application directly to weeds or their locus or can be concentrates or formulations which are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, and the like. Water is generally the carrier of choice for the dilution of concentrates.

Suitable solid carriers include talc, pyrophyllite clay, silica, attapulgus clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with a carrier before application. The surface-active agents can be anionic, cationic or nonionic in character and can be employed as emulsifying agents, wetting agents, suspending agents, or for other purposes. Typical surface-active agents include salts of alkyl sulfates, such as diethanolammonium lauryl sulfate; alkylarylsulfonate salts, such as calcium dodecylbenzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalenesulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethylammonium chloride; polyethylene glycol esters of fatty acids, such as polyethylene glycol stearate; block copolymers of ethylene oxide and propylene oxide; and salts of mono and dialkyl phosphate esters.

Other adjuvants commonly utilized in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea, and the like.

The concentration of the active ingredients in the herbicidal compositions of this invention is generally from about 0.001 to about 98 percent by weight. Concentrations from about 0.01 to about 90 percent by weight are often employed. In compositions designed to be employed as concentrates, the active ingredient is generally present in a concentration from about 5 to about 98 weight percent, preferably about 10 to about 90 weight percent. Such compositions are typically diluted with an inert carrier, such as water, before application. The diluted compositions usually applied to weeds or the locus of weeds generally contain about 0.0001 to about 1 weight percent active ingredient and preferably contain about 0.001 to about 0.05 weight percent.

The present compositions can be applied to weeds or their locus by the use of conventional ground or aerial dusters, sprayers, and granule applicators, by addition to irrigation water, and by other conventional means known to those skilled in the art.

EXAMPLES

The following Examples are presented to illustrate the various aspects of this invention and should not be construed as limitations to the claims.

1. Preparation of 3-Chloro-2-fluorothioanisole

A solution of 10 g (grams) (76 mmol (millimoles)) of 1-chloro-2-fluorobenzene in 75 mL (milliliters) of dry tetrahydrofuran (THF) was cooled with a dry ice/acetone bath and 34 mL (84 mmol) of 2.5M butyllithium was added dropwise under a nitrogen blanket over 45 min with stirring and cooling. The resulting solution was stirred for 2 hours at −78° C. A solution of 8.1 mL (91 mmol) of dimethyl disulfide in 10 mL of dry THF was added with stirring over a 30-min period keeping the temperature below −65° C. The mixture was allowed to warm to ambient temperature for 1 hour. It was then diluted with 75 mL of water. The resulting mixture was extracted with diethyl ether and the ether extract was dried over sodium sulfate and concentrated by evaporation under reduced pressure to obtain a yellow oil. This oil was purified by flash chromatography on 230–400 mesh silica gel eluting with a hexane/ethyl acetate mixture to obtain 9.0 g (69 percent of theory) of the title compound as a light yellow oil.

Elemental Analysis $C_7H_6ClFS$; Calc.: % C, 47.6; % H, 3.42; % S, 18.2; Found: % C, 47.5; % H, 3.32; % S, 18.2 $^1H$ NMR($CDCl_3$): 7.12(m, 3H), 2.47(s, 3H).

2. Preparation of 4-Bromo-3-chloro-2-fluorothioanisole

A solution of 4.0 g (23 mmol) of 3-chloro-2-fluorothioanisole in 50 mL of dichloromethane was prepared and a catalytic amount (0.15 g, 1.2 mmol) of ferric chloride and 1.5 mL (30 mmol) of bromine were added. The mixture was heated to 40° C. with stirring for 2 hours. The solution was then cooled to ambient temperature and 20 mL of dilute aqueous sodium bisulfite was added. The mixture was stirred until the dichloromethane layer was colorless (15 min). The organic phase was recovered and the aqueous phase was extracted with more dichloromethane. The organic phase and extract were combined and dried over sodium sulfate. The volatiles were removed by evaporation under reduced pressure to obtain 5.0 g (85 percent of theory) of the title compound as a tan oil.

$^1H$ NMR($CDCl_3$): 7.35(d, 1H, 7.2 Hz), 7.01(d, 1H, J=7.2 Hz), 2.44(s, 3H).

3. Preparation of 4-Bromo-3-chloro-2-fluoromethylsulfonylbenzene

Hydrogen peroxide (4.0 mL of 30 percent) was added with stirring to a solution of 5.0 g (20 mmol) of 4-bromo-3-chloro-2-fluorothioanisole in 50 mL of acetic acid. The mixture was heated at 50° C. for 3 hours and then cooled to ambient temperature. Most of the acetic acid was removed by evaporation under reduced pressure and the residue was diluted with water and extracted with dichloromethane. The extract was dried over sodium sulfate and concentrated by evaporation under reduced pressure to obtain 4.5 g (78 percent of theory) of the title compound as a white solid melting at 149° C.

Elemental Analysis $C_7H_5BrClFO_2S$; Calc.: % C, 29.2; % H, 1.75; % S, 11.1; Found: % C, 29.3; % H, 1.83; % S, 11.2 $^1H$ NMR($CDCl_3$): 7.7(m, 2H), 3.23(s, 3H).

4. Preparation of 2-Chloro-3-fluoro-4-methylsulfonylbenzoic Acid

A solution of 23 g (80 mmol) of 4-bromo-3-chloro-2-fluoromethylsulfonyl benzene in 100 mL of methanol was placed in a 300 mL stirred Parr bomb reactor and nitrogen was bubbled through the solution for 15 min. Triethylamine (28 mL, 200 mmol), palladium (II) acetate (0.90 g, 4.0 mmol), and 1,4-bis(diphenylphosphino)butane (3.4 g, 8.0 mmol) were then added and the bomb was sealed. The sealed bomb was charged with 300 psig (21,700 kiloPascals) of carbon monoxide and heated to 95° C. for 15 hours. The resulting solution was concentrated by evaporation under reduced pressure to remove the volatiles and the resulting slurry was diluted with 150 mL of 2N aqueous sodium hydroxide and stirred for 2 hr. The homogenous aqueous solution obtained was washed with dichloromethane and acidified with 2N aqueous hydrochloric acid. The resulting solution was extracted with ethyl acetate and the extract was dried over sodium sulfate and concentrated by evaporation under reduced pressure to obtain 10 g (63 percent of theory) of the title compound as a white solid melting at 204° C.

Elemental Analysis $C_8H_6ClFO_4S$; Calc.: % C, 38.0; % H, 2.39; % S, 12.7; Found: % C, 38.3; % H, 2.50; % S, 12.3 $^1H$ NMR(CDCl$_3$): 3.43(s, 3H) 7.88(m, 2H).

5. Preparation of 2,3-Difluoro-4-mothylsulfonylbenzoic Acid

A 2.5M solution of butyllithium in hexane (4.5 mL, 11 mmol) was added dropwise with stirring to a solution of 1.00 mL (10.2 mmol) of 1,2-difluorobenzene in 10 mL of dry tetrahydrofuran cooled to −70° C. under a nitrogen atmosphere. After 10 min, 0.80 mL (11 mmol) of dimethyl sulfide was added dropwise with stirring. Another 11 mmol of 2.5M butyllithium was then added and, after 10 min, the reaction mixture was quenched by bubbling a stream of dry carbon dioxide into the solution. The resulting mixture was diluted with water and the mixture was washed with ether and then acidified with 1N aqueous hydrochloric acid. The resulting heavy white precipitate was recrystallized from a mixture of ethyl acetate and heptane to obtain 0.65 g (31 percent of theory) of the title compound as a white solid melting at 214–215° C.

Elemental Analysis $C_8H_6F_2O_2S$; Calc.: % C, 47.1; % H, 2.96; Found: % C, 47.1; % H, 3.07 $^1H$ NMR(DMSO-d$_6$): 7.65(m, 1H), 7.22(m, 1H), 2.57(s, 3H).

6. Preparation of 3-Dimethylamino-2-methyl-4-methylsulfonylbenzoic Acid

Sodium borohydride (1.4 g, 36 mmol) was carefully added to a suspension of 1.53 g (6.30 mmol) of 3-methylamino-2-methyl-4-methylsulfonylbenzoic acid and 1.8 g (60 mmol) of paraformaldehyde in 75 mL of dry tetrahydrofuran under a nitrogen atmosphere. A 30 mL aliquot of trifluoroacetic acid was then added dropwise over 1 hour. Gas evolution was vigorous at first, but then subsided as the grey-white suspension was allowed to stir at room temperature. After 8 hours, the reaction was found to be complete by high pressure liquid chromatographic analysis (HPLC). The mixture was poured into 90 mL of a 25 percent aqueous sodium hydroxide solution containing ice, diluted with water and washed with ethyl acetate. The aqueous solution was then acidified with concentrated aqueous hydrochloric acid and the resulting mixture was extracted with ethyl acetate. The organic extract was mixed with dilute aqueous sodium bicarbonate solution and the aqueous phase was collected, acidified with 1N aqueous hydrochloric acid, and extracted with ethyl acetate. The organic extract obtained was dried over sodium sulfate and concentrated by evaporation under reduced pressure. The resulting residue was purified by flash column chromatography on silica gel, eluting with a 1:1 mixture of ethyl acetate and petroleum ether containing 1 percent acetic acid, to obtain 1.49 g (92 percent of theory) of the title compound as a yellow syrup which solidified on standing and melted at 113–114° C.

Elemental Analysis $C_{11}H_{15}O_4S$; Calc.: % C, 51.4; % H, 5.88; % N, 5.44; Found: % C, 51.0; % H, 6.39; % N, 5.36 $^1H$ NMR(CDCl$_3$): 8.00(d, 1H, J=8.4 Hz), 7.92(d, 1H, J=8.4 Hz), 3.29(s, 3H), 3.10(s, 6H), 2.59(s, 3H).

7. Preparation of 2-Chloro-3-(2-methoxyethylamino)-4-methylsulfonylbenzoic Acid

A solution of 5.0 g (19 mmol) of 2,3-dichloro-4-methylsulfonylbenzoic acid in 50 mL of 60 percent aqueous 2-methoxyethylamine was heated at reflux with stirring for 4 days. The dark mixture was then acidified with aqueous hydrochloric acid and extracted with dichloromethane. The extract was dried over magnesium sulfate and concentrated by evaporation under reduced pressure to obtain 8 g of the title compound as an impure dark oil. A 5.7 g portion of the this was converted to the methyl ester by refluxing overnight in 100 mL of a 50:1 mixture of methanol and concentrated sulfuric acid. The volatiles were removed by evaporation under reduced pressure and the residue obtained was partitioned between diethyl ether and water. The ethereal phase was dried over magnesium sulfate and concentrated by evaporation under reduced pressure. The residue was purified by flash column chromatography eluting with a mixture of ethyl acetate and hexane. The product fractions were then hydrolyzed by heating with stirring in 70 mL of a 5:2 mixture of methanol and iN aqueous sodium hydroxide solution. The methanol was removed by evaporation under reduced pressure. The aqueous residue was washed with diethyl ether, acidified with concentrated hydrochloric acid and extracted with dichloromethane. The dichloromethane extract was dried over magnesium sulfate and concentrated by evaporation under reduced pressure to obtain 2.8 g the title compound as a light green solid.

$^1H$ NMR(CDCl$_3$): 8.75(bs, 1H), 7.91(d, 1H, J=8.2 Hz), 7.40(d, 1H, J=8.2 Hz), 3.65(m, 4H), 3.41(s, 3H), 3.24(s, 3H).

8. Preparation of 2-Chloro-3-(3-methylpiperidin-1-yl)-4-methylsulfonylbenzoic Acid A solution of 3.0 g (12 mmol) of 2-chloro-3-fluoro-4-methylsulfonylbenzoic acid in 15 mL of 3-methylpiperidine was heated at 70° C. with stirring for 6 days. The reaction mixture was diluted with aqueous hydrochloric acid and extracted with dichloromethane. The organic extract was dried over magnesium sulfate and the solvent was removed by concentration under reduced pressure. The residue obtained was crystallized from acetonitrile to obtain 2.4 g (60 percent of theory) of the title compound as a solid.

$^1H$ NMR(CDCl$_3$): 8.08(d, 1H, J=9 Hz) 7.76(d, 1H, J=9 Hz), 3.52(m, 1H), 3.35(s, 1H), 3.20(m, 1H), 2.90(m, 2H), 1.80(m, 4H), 1.05(m, 1H), 0.85(d, 3H, J=5 Hz).

9. Preparation of 2-Chloro-4-methylsulfonyl-3-(pyrazol-1-yl)benzoic Acid

Pyrazole (210 mg, 3.09 mmol) was added to 190 mg (4.75 mmol) of 60 percent oil dispersed sodium hydride suspended in 7 mL of dry dimethylformamide. After the gas evolution had subsided, 500 mg (1.98 mmol) of 2-chloro-3-fluoro-4-methylsulfonylbenzoic acid was added and the mixture was stirred at 50° C. overnight. The mixture was then concentrated by evaporation under reduced pressure and the residue was partitioned between ethyl acetate and 1N aqueous hydrochloric acid. The aqueous phase was extracted with ethyl acetate. The organic phases were combined and extracted with dilute aqueous sodium bicarbonate solution. The aqueous extract was acidified with 1N aqueous hydrochloric acid and extracted with dichloromethane. The organic extract was concentrated by evaporation under reduced pressure. The crystalline residue obtained was purified by rinsing with ethyl acetate to obtain 540 mg (91 percent of theory) of the title compound as a white powder.

Elemental Analysis $C_{11}H_9ClN_2O_4S$; Calc.: % C, 43.9; % H, 3.02; % N, 9.32; Found: % C, 43.9; % H, 2.97; % N, 9.18
$^1$H NMR(CDCl$_3$): 8.16(d, 1H, J=8.2 Hz), 8.08(d, 1H, J=8.2 Hz), 7.82(d, 1H, J=2.0 Hz), 7.71(d, 1H, J=2.5 Hz), 6.57(dd, 1H, J=2.0 & 2.5 Hz), 3.02(s, 3H).

10. Preparation of 2-Chloro-3-(4-methoxypiperidin-1-yl)-4-methylsulfonylbenzoic Acid 2-Chloro-3-(4-hydroxypiperidin-1-yl)-4-methylsulfonylbenzoic acid (0.70 g, 2.1 mmol) was added with stirring to a suspension of 0.25 g (6.3 mmol) of sodium hydride in a mixture of 0.40 mL (6.4 mmol) of methyl iodide and 10 mL of dry tetrahydrofuran. The mixture was heated to reflux and stirred for 24 hr. The resulting mixture was treated with water, acidified with 1N aqueous hydrochloric acid and extracted several times with dichloromethane. The organic layers were combined and dried over magnesium sulfate, the solvent was removed by concentration under reduced pressure, and the residue was rinsed with petroleum ether to obtain 0.70 g (96 percent of theory) of the title compound.

11. Preparation of 1-Ethyl-4-(2,3-dichloro-4-methylsulfonylbenzoyl)-5-hydroxypyrazole A solution of 500 mg (1.85 mmol) of 2,3-dichloro-4-methylsulfonylbenzoic acid and 240 mg (2.14 mmol) of 1-ethyl-5-hydroxypyrazole in 10 mL of dry acetonitrile was treated with 430 mg (2.08 mmol) of dicyclohexylcarbodiimide with stirring at ambient temperature for 0.5 hr. The precipitate that formed was removed by filtration and the filtrate was treated with 0.5 mL of triethylamine and 1 mL of acetone cyanohydrin. After 1 hr, the reaction mixture was partitioned between dichloromethane and 1N aqueous hydrochloric acid. The organic layer was extracted with dilute aqueous sodium bicarbonate solution and the basic aqueous solution obtained was acidified with dilute aqueous hydrochloric acid and extracted with dichloromethane. The organic extract was dried over sodium sulfate and concentrated by evaporation under reduced pressure to obtain 540 mg (81 percent of theory) of the title compound as an orange syrup.

$^1$H NMR(CDCl$_3$): 8.20(d, 1H, J=8.0 Hz), 7.52(d, 1H, J=8.0 Hz), 7.31(s, 1H), 4.05(q, 2H, J=7.3 Hz) 3.34(s, 3H), 1.45(t, 3H, J=7.3 Hz)

12. Preparation of 1-(1,1-Dimethylethyl)-4-(2-chloro-3-(3-methylpiperidino-1-yl)-4-methylsulfonylbenzoyl)-5-hydroxypyrazole (Compound 62)

A solution of 0.80 g (2.4 mmol) of 2-chloro-3-(3-methylpiperidino-1-yl)-4-methylsulfonylbenzoic acid in mixture of 2.5 mL of thionyl chloride and 2.5 mL of dichloromethane was heated at reflux with stirring for 1.5 hour. The volatile components were removed by concentration under reduced pressure and the residue was dissolved in a few mL of dichloromethane. The resulting solution was added to a solution of 0.7 g (4.7 mmol) of 1-(1,1-dimethylethyl)-5-hydroxypyrazole in a mixture of 3 mL of dichloromethane and 1 mL of triethylamine. After a few minutes, the reaction mixture was diluted with dichloromethane, washed with water, washed with dilute aqueous sodium bicarbonate, and dried over magnesium sulfate. The volatiles were removed by concentration under reduced pressure and the residue was dissolved in a few mL of dry acetonitrile. The resulting solution was treated with excess triethylamine and 10 drops of acetone cyanohydrin. After stirring at ambient temperature for 18 hr, the mixture was diluted with water, washed with diethyl ether, and acidified with hydrochloric acid. The resulting mixture was extracted with dichloromethane and the extract was dried over magnesium sulfate and concentrated by evaporation under reduced pressure. The resulting residue was recrystallized from ethanol to obtain 0.27 g (25 percent of theory) of the title compound as an off-white solid.

13. Preparation of 1-Ethyl-4-(2-chloro-3-dimethylamino-4-methylsulfonylbenzoyl)-5-hydroxypyrazole (Compound 1)

A mixture of 0.60 g (1.7 mmol) of 1-ethyl-4-(2,3-dichloro-4-methylsulfonylbenzoyl)-5-hydroxypyrazole and 8 mL of 40 percent aqueous dimethylamine was placed in a pressure reactor and heated at 110° C. for 24 hours. It was then allowed to cool and was concentrated by evaporation under reduced pressure. The residue was dissolved in dichloromethane and the solution obtained was washed with 1N aqueous hydrochloric acid, dried over sodium sulfate, and concentrated by evaporation under reduced pressure to obtain about 0.50 g of a yellow foam. This was crystallized from ethanol to obtain, after drying for 24 hours at 50° C., 0.17 g of the title compound as an off-white solid melting at 227–228° C. with decomposition.

Elemental Analysis $C_{15}H_{18}ClN_3O_4S$; Calc.: % C, 48.6; % H, 4.88; % N, 11.3; % S, 8.62; Found: % C, 48.7; % H, 5.08; % N, 11.4; % S, 8.35.

14. Preparation of 1-Ethyl-4-(2-chloro-3-(morpholin-4-yl)-4-methylsulfonylbenzoyl)-5-hydroxypyrazole (Compound 23)

A solution of 1.5 g (4.1 mmol) of 1-ethyl-4-(2,3-dichloro-4-methylsulfonylbenzoyl)-5-hydroxypyrazole in 30 mL of morpholine was heated at 100° C. with stirring for 2 days. The reaction mixture was then diluted with water, washed with diethyl ether, and acidified with hydrochloric acid. The resulting solution was extracted with dichloromethane and the extract was concentrated by evaporation under reduced pressure. The resulting residue was recrystallized from ethanol/dichloromethane to obtain to 0.33 g (20 percent of theory) of the title compound as a white solid.

15. Preparation of 1-Ethyl-4-(2-chloro-3-(3,5-dimethylpyrazol-1-yl)-4-methylsulfonylbenzoyl)-5-hydroxypyrazole (Compound 67)

3,5-Dimethylpyrazole (215 mg, 2.23 mmol) was added to a suspension of 150 mg (3.75 mmol) of 60 percent oil dispersed sodium hydride in 6 mL of dry dimethylformamide. After gas evolution had subsided, 500 mg (1.45 mmol) of 1-ethyl-4-(2-chloro-3-fluoro-4-methylsulfonylbenzoyl)-5-hydroxypyrazole was added and the mixture was stirred at 50° C. overnight. The reaction mixture was concentrated by evaporation under reduced pressure and partitioned between dichloromethane and 1N aqueous hydrochloric acid. The aqueous phase was extracted with additional dichloromethane. The organic layers were combined and extracted with dilute aqueous sodium bicarbonate. The aqueous extract was acidified with 1N aqueous hydrochloric acid and the resulting mixture was extracted with ethyl acetate. The solvent was removed from the organic extract by evaporation under reduced pressure and the crystalline residue obtained was purified by rinsing with diethyl ether to obtain 360 mg (59 percent of theory) of the title compound as a white powder melting at 217–218° C.

16. Preparation 1-Ethyl-4-(2-chloro-3-(2-hydroxybutylamino)-4-methylsulfonylbenzoyl)-5-hydroxypyrazole A suspension of 5.20 g (14.3 mmol) of 1-ethyl-4-(2,3-dichloro-4-methylsulfonylbenzoyl)-5-hydroxypyrazole in 7 mL of 1-amino-2-butanol was heated with stirring at 100° C. for 1 day. The volatile components of the resulting mixture were removed by evaporation under reduced pressure with mild heating and the residue was dissolved in 150 mL of a 2:1 mixture ethanol and water. A few grams of potassium hydroxide were added and the mixture was heated with stirring at 100° C. for 5 hours. It was then acidified with dilute aqueous hydrochloric acid and extracted with dichloromethane. The organic extract was dried over sodium sulfate and the solvent was removed by evaporation under reduced pressure to obtain 5.04 g (85 percent of theory) of the title compound as a yellow foam. A portion of this was purified by recrystallization from ethanol to obtain a yellow powder melting at 153–154° C.

Elemental Analysis $C_{17}H_{22}ClN_3O_5S$; Calc.: % C, 49.1; % H, 5.33; % N, 10.1; Found: % C, 49.2; % H, 5.40; % N, 9.97
$^1H$ NMR(CDCl$_3$): 7.92(d, 1H, J=8.0 Hz), 7.35(s, 1H), 7.04(d, 1H, J=8.0 Hz), 4.08(q, 2H, J=7.3 Hz) 3.76(m, 2H), 3.30(m, 1H), 3.25(s, 3H), 1.58(m, 2H), 1.45(t, 3H, J=6.9 Hz), 1.02(t, 3H, J=7.8 Hz).

17. Preparation of 1-Ethyl-4-(2-chloro-3-(tetrahydro-1,3-oxazin-3-yl)-4-methylsulfonylbenzoyl)-5-hydroxypyrazole (Compound 54)

A solution of 350 mg (0.87 mmol) of 1-ethyl-4-(2-chloro-3-(3-hydroxypropylamino)-4-methylsulfonylbenzoyl)-5-hydroxypyrazole in 1 mL of dichloromethane was diluted with 10 mL of diethyl ether and treated with 0.10 mL (1.3 mmol) of formalin. After stirring for 40 hours at ambient temperature, the reaction mixture contained a white precipitate and approximately one third of the starting material remained according to HPLC analysis. The solution was decanted and the solids remaining were dissolved in dichloromethane. The resulting solution was washed with water, dried over sodium sulfate, and concentrated by evaporation under reduced pressure. The residue was recrystallized from ethyl acetate to obtain 160 mg (43 percent of theory) of the title compound as tan crystals.

18. Preparation of 1-Ethyl-4-(2-chloro-3-(morpholin-2-on-4-yl)-4-methylsulfonylbenzoyl)-5-hydroxypyrazole A solution of 0.50 g (1.3 mmol) of 1-ethyl-4-(2-chloro-3-(2-hydroxyethylamino)-4-methylsulfonylbenzoyl)-5-hydroxypyrazole in 20 mL of toluene was heated to 90° C. and treated with 2 mL of 40 percent aqueous glyoxal solution with stirring. The progress of the reaction was monitored by HPLC analysis and additional aliquots of 40 percent aqueous glyoxal solution were added every few hours until the starting material was consumed. After 24 hours, the reaction was complete and the dark solution was decanted from a gummy residue. The residue was extracted with several portions of hot toluene and the organic solutions were combined. The volatiles were removed by evaporation under reduced pressure and the resulting residue was purified by adding a small amount of diethyl ether and collecting the solids present by filtration. More solids were obtained when the diethyl other solution was concentrated by evaporation. These solids were collected by filtration as well. The solids were combined to obtain 0.39 g (71 percent of theory) of the title compound as a tan powder melting at 198–202° C.

Elemental Analysis $C_{17}H_{18}ClN_3O_6S$; Calc.: % C, 47.7; % H, 4.24; % N, 9.82 Found: % C, 47.5; % H, 4.49; % N, 9.74
$^1H$ NMR(CDCl$_3$): 8.12(d, 1H, J=6.2 Hz), 7.54(d, 1H, J=6.2 Hz), 4.74(td, 1H, J=3.6, 9.7 and 13 Hz) 4.55(d, 1H, J=17 Hz), 4.48(dt, 1H, J=3.6, 7.2 and 11 Hz), 4.04(q, 2H, J=7.3 Hz), 3.90(d, 1H, J=17 Hz), 3.82(m, 1H), 3.34(m, 1H), 3.26(s, 3H), 1.45(t, 3H, J=7.3 Hz).

19. Preparation of 1-Ethyl-4-(2-chloro-3-(2-hydroxymorpholin-4-yl)-4-methylsulfonylbenzoyl)-5-hydroxypyrazole A solution of 1.38 g (3.22 mmol) of 1-ethyl-4-(2-chloro-3-(morpholin-2-on-4-yl)-4-methylsulfonylbenzoyl)-5-hydroxypyrazole in 200 mL of dichloromethane was cooled to −78° C. and treated dropwise with stirring with 7.0 ml, (7.0 mmol) of a 1M solution of diisobutylaluminum hydride in dichloromethane. After 15 min, the reaction was quenched with 5 mL of methanol and 100 mL of 1N aqueous hydrochloric acid and was then allowed to warm to room temperature with vigorous stirring for 30 min. The layers were separated and the aqueous layer was washed with dichloromethane. The organic layers were combined and concentrated by evaporation under reduced pressure. The residue was dissolved in a mixture of acetonitrile and 1N aqueous hydrochloric acid. The mixture was stirred for a few minutes and was then diluted with dichloromethane. The solution obtained was washed with water, dried over sodium sulfate, and concentrated by evaporation under reduced pressure. The resulting solid residue was extracted with ethanol and dried to obtain 1.20 g (87 percent of theory) of the title compound as a tan powder melting at 209–210° C.

Elemental Analysis $C_{17}H_{20}ClN_3O_6S$; Calc.: % C, 47.5; % H, 4.69; % N, 9.77; Found: % C, 47.3; % H, 4.60; % N, 9.52
$^1H$ NMR(CDCl$_3$): 8.12(dd, 1H, J=7.0 Hz), 7.48(dd, 1H, J=7.0 Hz), 7.32(bs, 1H), 5.22 & 5.02(bs & bd, 1H), 4.42(bt, 1H), 4.50(m, 3H), 3.88(bd, 1H), 3.66(m, 1H) 3.46 & 3.32(s & s, 3H), 3.05(bd, 1H), 2.85(bd, 1H), 1.48(t, 3H, J=7 Hz); Mass Spectrum: m/z 428 (M−H).

20. Preparation of 1-Ethyl-4-(2-chloro-3-(2-ethylmorpholin-4-yl)-4-methylsulfonylbenzoyl)-5-hydroxypyrazole (Compound 83)

A solution of 500 mg (1.09 mmol) of 1-ethyl-4-(2-chloro-3-(6-ethyl-2-hydroxymorpholin-4-yl)-4-methylsulfonylbenzoyl)-5-hydroxypyrazole in 3 mL of trifluoroacetic acid was treated with 1 mL of triethylsilane at ambient temperature and stirred vigorously for 2 hours. The solvent was removed by evaporation under reduced pressure and the orange residue obtained was partitioned between dichloromethane and water. The organic solution was dried over sodium sulfate and concentrated by evaporation under reduced pressure. The solid residue was recrystallized from ethanol to obtain 210 mg (44 percent of theory) of the title compound as light orange-brown crystals.

21. Preparation of 1-Ethyl-4-(2-chloro-3-(6-ethyl-2-methoxymorpholin-4-yl)-4-methylsulfonylbenzoyl)-5-hydroxypyrazole (Compounds 84 and 85)

A solution of 1.08 g (2.35 mmol) of 1-ethyl-4-(2-chloro-3-(2-hydroxy-6-ethylmorpholin-4-yl)-4-methylsulfonylbenzoyl)-5-hydroxypyrazole in 5 mL of methanol was added with stirring to a solution of 20 mL of methanol pre-treated with 2 mL of acetyl chloride. After 1 hour, the mixture was diluted with dichloromethane and the resulting solution was washed with water and concentrated by evaporation under reduced pressure. The two component mixture residue obtained was separated and purified by preparative reverse-phase HPLC eluting with 1:1 acetonitrile/water containing 0.1 percent phosphoric acid. The fractions containing each of the two products were combined separately, concentrated by evaporation under reduced pressure and extracted with dichloromethane. The dichloromethane solutions were dried over sodium sulfate and concentrated by evaporation under reduced pressure to obtain the title compound as cis and trans isomers, both as syrups. There was 294 mg (27 percent of theory) of the more polar cis compound and 548 mg (49 percent of theory) of the less polar trans compound. These syrups were separately crystallized from ethanol to obtain the cis and trans isomers of the title compound as brown and off-white crystals, respectively.

22. Evaluation of Postemergence Herbicidal Activity

Seeds of the desired test plant species were planted in Grace-Sierra MetroMix® 306 planting mixture, which typically has a pH of 6.0 to 6.8 and an organic matter content of about 30 percent, in plastic pots with a surface area of 64 square centimeters. When required to ensure good germination and healthy plants, a fungicide treatment and/or other chemical or physical treatment was applied. The plants were grown for 7–21 days in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The plants were employed for testing when they reached the first or second true leaf stage.

A weighed amount, determined by the highest rate to be tested, of each test compound was placed in a 20 mL glass vial and was dissolved in 4 mL of a 97:3 v/v (volume/volume) mixture of acetone and dimethyl sulfoxide to obtain concentrated stock solutions. If the test compound did not dissolve readily, the mixture was warmed and/or sonicated. The concentrated stock solutions obtained were diluted with an aqueous mixture containing acetone, water, isopropyl alcohol, dimethyl sulfoxide, Atplus 411F crop oil concentrate, and Triton X-155 surfactant in a 48.5:39:10:1.5:1.0:0.02 v/v ratio to obtain spray solutions of known concentration. The solutions containing the highest concentration to be tested were prepared by diluting 2 mL aliquots of the stock solution with 13 mL of the mixture and lower concentrations were prepared by dilution of appropriate smaller portions of the stock solution. Approximately 1.5 mL aliquots of each solution of known concentration were sprayed evenly onto each of the test plant pots using a DeVilbiss atomizer driven by compressed air pressure of 2 to 4 psi (140 to 280 kiloPascals) to obtain thorough coverage of each plant. Control plants were sprayed in the same manner with the aqueous mixture. In this test an application rate of 1 ppm results in the application of approximately 1 g/Ha.

The treated plants and control plants were placed in a greenhouse as described above and watered by sub-irrigation to prevent wash-off of the test compounds. After 2 weeks the condition of the test plants as compared with that of the untreated plants was determined visually and scored on a scale of 0 to 100 percent where 0 corresponds to no injury and 100 corresponds to complete kill. Some of the compounds tested, application rates employed, plant species tested, and results are given in Table 2.

TABLE 2

POSTMERGENCE HERBICIDAL ACTIVITY

| Cpd. No. | Rate, ppm | BWCHK | BWCKB | BWLMQ | BWPIG | BWVEL | BWVIO | BWWBK | GWBLG | GWBRN | GWCRB | GWGFT | GWROX | GWWOT |
|---|---|---|---|---|---|---|---|---|---|---|---|---|---|---|
| 1 | 15.6 | 99 | 98 | 100 | 100 | 80 | 78 | 60 | 15 | 98 | 98 | 75 | 100 | 60 |
| 2 | 31.3 | 70 | 80 | 98 | 100 | 75 | 80 | 95 | 20 | 85 | 80 | 90 | 100 | 40 |
| 3 | 31.3 | 85 | 85 | 100 | 100 | 90 | 90 | 100 | 30 | 88 | 88 | 60 | 90 | 78 |
| 4 | 15.6 | 80 | 90 | 90 | 90 | 85 | 80 | 90 | 45 | 80 | 90 | 80 | 95 | 60 |
| 5 | 31.3 | 65 | 80 | 98 | 100 | 78 | 78 | 95 | 30 | 90 | 85 | 80 | 100 | 55 |
| 6 | 31.3 | 78 | 80 | 95 | 78 | 78 | 80 | 80 | 20 | 95 | — | 70 | 100 | 20 |
| 7 | 7.88 | 80 | 70 | 90 | 90 | 80 | 45 | 60 | 30 | 90 | — | 78 | 95 | 40 |
| 8 | 3.9 | 70 | 95 | 95 | 78 | 95 | 95 | 40 | 20 | 90 | — | 65 | 95 | 55 |
| 9 | 15.6 | 85 | 100 | 100 | 90 | 90 | 50 | 85 | 40 | 88 | — | 80 | 85 | 30 |
| 10 | 7.8 | 85 | 95 | 100 | 70 | 85 | 95 | 80 | 50 | 85 | — | 80 | 90 | 70 |
| 11 | 7.8 | 80 | 90 | 95 | 95 | 90 | 98 | 90 | 50 | 90 | 98 | 85 | 100 | 60 |
| 12 | 31.3 | 80 | 90 | 100 | 98 | 80 | 75 | 80 | 45 | 95 | 85 | 98 | 90 | 85 |
| 13 | 15.6 | 75 | 85 | 100 | 98 | 95 | 95 | 90 | 35 | 98 | 80 | 95 | 95 | 50 |
| 14 | 7.8 | 85 | 90 | 100 | 98 | 85 | 70 | 90 | 30 | 90 | 85 | 90 | 90 | 65 |
| 15 | 7.8 | 95 | 85 | 100 | 95 | 85 | 55 | 80 | 25 | 90 | 80 | 80 | 85 | 75 |
| 16 | 15.6 | 98 | 80 | 100 | 95 | 95 | 55 | 95 | 40 | 95 | 80 | 80 | 78 | 55 |
| 17 | 31.3 | 80 | 90 | 100 | 100 | 90 | 55 | 95 | 40 | 95 | 80 | 70 | 75 | 45 |
| 18 | 31.3 | 95 | 80 | 100 | 95 | 75 | 78 | 80 | 55 | 95 | 90 | 90 | 95 | 70 |
| 19 | 7.8 | 90 | 85 | 100 | 80 | 90 | 45 | 78 | 0 | 90 | 90 | 78 | 80 | 50 |
| 20 | 15.6 | 90 | 90 | 100 | 90 | 78 | 70 | 65 | 50 | 95 | 50 | 80 | 95 | 78 |
| 21 | 7.8 | 100 | 95 | 95 | 80 | 80 | 45 | 45 | 20 | 95 | 75 | 90 | 95 | 20 |
| 22 | 7.8 | 85 | 90 | 100 | 95 | 70 | 55 | 40 | 45 | 95 | 90 | 90 | 95 | 65 |
| 23 | 3.9 | 90 | 90 | 100 | 80 | 65 | 25 | 20 | 70 | 95 | 100 | 90 | 100 | 80 |
| 24 | 31.3 | 100 | 95 | 100 | 95 | 80 | 90 | 95 | 55 | 100 | 78 | 70 | 95 | 55 |
| 25 | 62.5 | 85 | 80 | 100 | 55 | 70 | 70 | 60 | 20 | 95 | 85 | 80 | 80 | 80 |
| 26 | 31.3 | 80 | 90 | 100 | 80 | 85 | 55 | 90 | 0 | 95 | 95 | 78 | 80 | 80 |
| 27 | 31.3 | 95 | 80 | 95 | 95 | 70 | 78 | 95 | 20 | 90 | 90 | 75 | 90 | 20 |
| 28 | 31.3 | 90 | 85 | 100 | 95 | 100 | 50 | 100 | 45 | 95 | 80 | 78 | 80 | 45 |
| 29 | 31.3 | 100 | 80 | 100 | 100 | 78 | 40 | 95 | 40 | 90 | 70 | 80 | 85 | 50 |
| 30 | 7.8 | 80 | 85 | 95 | 95 | 90 | 55 | 70 | 90 | 95 | 95 | 75 | 100 | 78 |
| 31 | 31.3 | 90 | 80 | 100 | 80 | 85 | 75 | 90 | 30 | 80 | 90 | 80 | 80 | 90 |
| 32 | 3.9 | 60 | 80 | 90 | 50 | 78 | 50 | 60 | 70 | 90 | 85 | 85 | 95 | 70 |
| 33 | 15.6 | 80 | 80 | 85 | 50 | 90 | 70 | 70 | 90 | 90 | 95 | 85 | 100 | 90 |
| 34 | 3.9 | 80 | 90 | 95 | 60 | 80 | 55 | 60 | 90 | 90 | 95 | 85 | 80 | 85 |
| 35 | 7.8 | 70 | 90 | 100 | 60 | 80 | 60 | 70 | 90 | 100 | 90 | 85 | 100 | 95 |
| 36 | 15.6 | 80 | 80 | 95 | 80 | 85 | 55 | 40 | 55 | 95 | 90 | 90 | 95 | 75 |
| 37 | 7.8 | 75 | 80 | 95 | 80 | 70 | 65 | 40 | 70 | 95 | 78 | 70 | 100 | 90 |
| 38 | 15.6 | 75 | 90 | 95 | 80 | 85 | 60 | 70 | 60 | 90 | 85 | 78 | 95 | 70 |
| 39 | 15.6 | 80 | 80 | 100 | 100 | 90 | 80 | 95 | 60 | 100 | 80 | 75 | 100 | 45 |
| 40 | 7.8 | 78 | 90 | 100 | 95 | 85 | 40 | 70 | 40 | 100 | 90 | 78 | 95 | 60 |
| 41 | 7.8 | 55 | 90 | 95 | 70 | 80 | 50 | 45 | 45 | 95 | 90 | 75 | 100 | 50 |
| 42 | 15.6 | 55 | 90 | 95 | 55 | 80 | 30 | 70 | 65 | 90 | 90 | 80 | 95 | 78 |
| 43 | 31.3 | 70 | 80 | 90 | 100 | 75 | 40 | 65 | 50 | 95 | 90 | 85 | 100 | 95 |
| 44 | 62.5 | 80 | 90 | 95 | 95 | 90 | 60 | 78 | 40 | 95 | 90 | 90 | 100 | 80 |
| 45 | 31.3 | 80 | 90 | 95 | 95 | 78 | 80 | 60 | 30 | 95 | 90 | 85 | 100 | 65 |
| 46 | 7.8 | 65 | 75 | 90 | 95 | 60 | 30 | 50 | 45 | 90 | 90 | 80 | 95 | 70 |

TABLE 2-continued

POSTMERGENCE HERBICIDAL ACTIVITY

| Cpd. No. | Rate, ppm | BWCHK | BWCKB | BWLMQ | BWPIG | BWVEL | BWVIO | BWWBK | GWBLG | GWBRN | GWCRB | GWGFT | GWROX | GWWOT |
|---|---|---|---|---|---|---|---|---|---|---|---|---|---|
| 47 | 31.3 | 60 | 80 | 95 | 70 | 70 | 60 | 65 | 75 | 90 | 90 | 80 | 100 | 90 |
| 48 | 31.3 | 78 | 90 | 85 | 60 | 80 | 30 | 60 | 45 | 90 | 90 | 90 | 100 | 80 |
| 49 | 31.3 | 80 | 80 | 90 | 95 | 90 | 50 | 70 | 40 | 85 | 85 | 85 | 90 | 78 |
| 50 | 31.3 | 70 | 85 | 95 | 80 | 95 | 60 | 80 | 75 | 95 | 85 | 90 | 90 | 90 |
| 51 | 15.6 | 78 | 80 | 95 | 90 | 85 | 30 | 70 | 40 | 80 | 90 | 55 | 95 | 78 |
| 52 | 62.5 | 70 | 90 | 95 | 90 | 80 | 55 | 65 | 30 | 90 | 90 | 80 | 80 | 30 |
| 53 | 15.6 | 75 | 85 | 90 | 70 | 75 | 20 | 45 | 55 | 90 | 78 | 95 | 100 | 70 |
| 54 | 31.3 | 90 | 80 | 100 | 95 | 95 | 65 | 70 | 70 | 90 | 80 | 60 | 80 | 80 |
| 55 | 125 | 80 | 85 | 90 | 90 | 90 | 75 | 65 | 40 | 90 | 70 | 80 | 90 | 50 |
| 56 | 31.3 | 60 | 80 | 90 | 90 | 75 | 70 | 20 | 45 | 90 | 90 | 85 | 95 | 100 |
| 57 | 62.5 | 80 | 85 | 90 | 95 | 80 | 78 | 78 | 30 | 90 | 78 | 80 | 100 | 70 |
| 58 | 31.3 | 90 | 90 | 90 | 100 | 95 | 80 | 78 | 60 | 90 | 90 | 95 | 100 | 80 |
| 59 | 31.3 | 90 | 90 | 90 | 85 | 80 | 95 | 78 | 60 | 95 | 85 | 80 | 95 | 95 |
| 60 | 62.5 | 70 | 88 | 85 | 60 | 75 | 80 | 80 | 60 | 85 | 80 | 80 | 90 | 85 |
| 61 | 125 | 70 | 70 | 85 | 85 | 75 | 70 | 50 | 50 | 80 | 80 | 80 | 95 | 95 |
| 62 | 125 | 80 | 88 | 80 | 60 | 85 | 85 | 70 | 70 | 85 | 80 | 85 | 90 | 95 |
| 63 | 62.5 | 85 | 80 | 85 | 80 | 70 | 90 | 85 | 70 | 88 | 80 | 70 | 80 | 88 |
| 65 | 62.5 | 85 | 85 | 90 | 80 | 85 | 80 | 80 | 75 | 90 | 90 | 85 | 90 | 95 |
| 66 | 15.6 | 80 | 80 | 90 | 90 | 80 | 55 | 50 | 60 | 95 | 85 | 95 | 95 | 88 |
| 67 | 125 | 70 | 80 | 90 | 95 | 85 | 60 | 50 | 50 | 95 | 90 | 90 | 60 | 100 |
| 68 | 7.8 | 80 | 80 | 100 | 78 | 80 | 40 | 45 | 45 | 85 | 90 | 90 | 90 | 100 |
| 69 | 125 | 90 | 95 | 100 | 100 | 30 | 90 | 30 | 10 | 95 | 90 | 90 | 50 | 30 |
| 70 | 125 | 80 | 95 | 100 | 30 | 30 | 90 | 40 | 30 | 85 | 90 | 90 | 10 | 30 |
| 71 | 62.5 | 80 | 85 | 90 | 10 | 50 | 90 | 30 | 50 | 95 | 85 | 85 | 90 | 85 |
| 72 | 62.5 | 70 | 85 | 95 | 70 | 70 | 80 | 40 | 50 | 90 | 50 | 70 | 60 | 20 |
| 73 | 15.6 | 50 | 70 | 95 | 95 | 70 | 85 | 20 | 0 | 95 | 60 | 55 | 95 | 60 |
| 74 | 62.5 | 85 | 90 | 95 | 100 | 80 | 40 | 50 | 50 | 95 | 70 | 100 | 98 | 50 |
| 75 | 31.3 | 50 | 70 | 90 | 85 | 50 | 20 | 60 | 0 | 40 | 70 | 85 | 85 | 70 |
| 76 | 62.5 | 75 | 85 | 95 | 100 | 70 | 70 | 40 | 50 | 90 | 70 | 95 | 98 | 35 |
| 77 | 7.8 | 60 | 90 | 90 | 75 | 95 | 30 | 30 | 20 | 100 | 70 | 90 | 85 | 98 |
| 78 | 15.6 | 60 | 80 | 98 | 80 | 75 | 75 | 75 | 70 | 25 | 80 | 98 | 98 | 75 |
| 79 | 15.6 | 95 | 85 | 95 | 95 | 55 | 0 | 55 | 80 | 95 | 85 | 90 | 90 | 95 |
| 80 | 62.5 | 70 | 80 | 98 | 80 | 45 | 40 | 40 | 30 | 90 | 90 | 98 | 90 | 98 |
| 81 | 62.5 | — | 85 | 95 | 100 | 60 | 50 | 35 | 70 | 98 | 85 | 70 | 90 | 95 |
| 82 | 31.3 | — | 85 | 95 | 98 | 80 | 30 | 20 | 80 | 90 | 75 | 90 | 98 | 98 |
| 83 | 15.6 | 40 | 80 | 85 | 98 | 70 | 20 | 60 | 75 | 90 | 95 | 98 | 98 | 95 |
| 84 | 15.6 | 45 | 75 | 70 | 98 | 75 | 70 | 0 | 80 | 90 | 90 | 95 | 90 | 90 |
| 85 | 15.6 | 20 | 80 | 80 | 70 | 20 | 30 | 40 | 90 | 90 | 85 | 40 | 98 | 90 |
| 86 | 7.8 | 90 | 80 | 90 | 70 | 70 | 30 | 50 | 75 | 95 | 90 | 85 | 95 | 90 |
| 87 | 62.5 | 80 | 95 | 95 | 70 | 78 | 70 | 100 | 90 | 85 | 60 | 78 | 85 | 100 |
| 88 | 15.6 | 80 | 80 | 90 | 80 | 75 | 0 | 90 | 78 | 85 | 95 | 80 | 100 | 95 |
| 89 | 7.8 | 80 | 85 | 90 | 90 | 80 | 0 | 90 | 50 | 90 | 80 | 80 | 100 | 90 |
| 90 | 31.3 | 80 | 90 | 95 | 50 | 80 | 50 | 60 | 90 | 85 | 80 | 90 | 95 | 80 |
| 91 | 62.5 | 80 | 80 | 95 | 45 | 90 | 55 | 65 | 70 | 80 | 50 | 80 | 78 | 95 |
| 92 | 62.5 | 40 | 80 | 80 | 20 | 60 | 50 | 40 | 45 | 78 | 30 | 30 | 50 | 78 |
| 93 | 62.5 | 50 | 80 | 80 | 20 | 80 | 20 | 70 | 80 | 85 | 80 | 80 | 95 | 95 |
| 95 | 62.5 | 55 | 70 | 90 | 90 | 55 | 40 | 20 | 60 | 90 | 80 | 90 | 85 | 45 |

TABLE 2-continued

| Cpd. No. | Rate, ppm | POSTMERGENCE HERBICIDAL ACTIVITY |||||||||||||
| --- | --- | --- | --- | --- | --- | --- | --- | --- | --- | --- | --- | --- | --- |
| | | BWCHK | BWCKB | BWLMQ | BWPIG | BWVEL | BWVIO | BWWBK | GWBLG | GWBRN | GWCRB | GWGFT | GWROX | GWWOT |
| 96 | 15.6 | 80 | 85 | 90 | 80 | 85 | 40 | 60 | 80 | 85 | 85 | 90 | 95 | 95 |

BWCHK = chickweed (*Stellaria media*)
BWCKB = cocklebur (*Xanthium strumarium*)
BWLMQ = lambsquarters (*Chenopodium album*)
BWPIG = pigweed (*Amaranthus retroflexus*)
BWVEL = velvetleaf (*Abutilion theophrasti*)
BWVIO = viola (*Viola tricolor*)
BWWBK = wild buckwheat (*Polygonum convolvulus*)
GWBLG = blackgrass (*Alopecurus myosuroides*)
GWBRN = barnyardgrass (*Echinochloa crus-galli*)
GWCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

23. Evaluation of Preemergence Herbicidal Activity

Seeds of the desired test plant species were planted in a soil matrix prepared by mixing a loam soil which was composed of about 43 percent silt, 19 percent clay, and 38 percent sand and had a pH of about 8.1 and an organic matter content of about 1.5 percent and sand in a 70 to 30 ratio. The soil matrix was contained in plastic pots with a surface area of 161 square centimeters. When required to ensure good germination and healthy plants, a fungicide treatment and/or other chemical or physical treatment was applied.

A weighed amount, determined by the highest rate to be tested, of each test compound was placed in a 20 mL glass vial and was dissolved in 8 mL of a 97:3 v/v (volume/volume) mixture of acetone and dimethyl sulfoxide to obtain concentrated stock solutions. If the test compound did not dissolve readily, the mixture was warmed and/or sonicated. The stock solutions obtained were diluted with a 99.9:0.1 mixture of water and Tween® 155 surfactant to obtain application solutions of known concentration. The solutions containing the highest concentration to be tested were prepared by diluting 4 mL aliquots of the stock solution with 8.5 mL of the mixture and lower concentrations were prepared by dilution of appropriate smaller portions of the stock solution. A 2.5 mL aliquot of each solution of known concentration was sprayed evenly onto the soil of each seeded pot using a Cornwall 5.0 mL glass syringe fitted with a TeeJet TN-3 hollow cone nozzle to obtain thorough coverage of the soil in each pot. Control pots were sprayed in the same manner with the aqueous mixture. A highest application rate of 4.48 Kg/Ha is achieved when 50 mg of test compound is employed.

The treated pots and control pots were placed in a greenhouse with an approximately 15 hr photoperiod which was maintained at about 23–29° C. during the day and 22–28° C. during the night. Nutrients and water were added on a regular basis and supplemental lighting was provided with overhead metal halide 1000 Watt lamps as necessary. The water was added by top-irrigation. After 3 weeks the condition of the test plants that germinated and grew as compared with that of the untreated plants that germinated and grew was determined visually and scored on a scale of 0 to 100 percent where 0 corresponds to no injury and 100 corresponds to complete kill or no germination. Some of the compounds tested, application rates employed, plant species tested, and results are given in Table 3.

TABLE 3

PREEMERGENCE HERBICIDAL ACTIVITY

| Cpd. No. | Rate, Kg/Ha | BWCKB | BWLMQ | BWPIG | BWVEL | BWWPT | GWBLG | GWBRN | GWCRB | GWGFT | GWROX | GWWOT |
|---|---|---|---|---|---|---|---|---|---|---|---|---|
| 1 | 0.070 | 65 | 100 | 95 | 100 | 55 | 50 | 100 | 100 | 25 | 100 | 20 |
| 2 | 0.035 | 50 | 100 | 90 | 100 | — | 0 | 99 | 100 | 90 | 100 | 30 |
| 3 | 0.070 | 100 | 100 | 100 | 100 | 50 | 40 | 100 | 100 | 65 | 100 | 45 |
| 4 | 0.070 | 100 | — | 100 | 100 | — | 45 | 75 | 100 | 90 | 100 | 40 |
| 5 | 0.14 | 90 | — | 100 | 100 | — | 40 | 100 | 100 | 95 | 100 | 50 |
| 6 | 0.56 | 100 | — | 100 | 100 | — | 0 | 95 | 100 | 90 | 100 | 20 |
| 7 | 0.070 | 85 | — | 100 | 100 | — | 10 | 100 | 100 | 99 | 100 | 45 |
| 8 | 0.070 | 100 | — | 100 | 100 | — | 20 | 70 | 100 | 60 | 100 | 20 |
| 9 | 0.035 | 80 | 100 | 100 | 100 | — | 30 | 30 | 100 | 50 | 100 | 20 |
| 10 | 0.035 | 60 | 100 | 100 | 100 | — | 30 | 100 | 100 | 95 | 100 | 40 |
| 11 | 0.070 | 100 | 100 | 100 | 100 | — | 20 | 78 | 100 | 100 | 100 | 20 |
| 12 | 0.14 | 100 | 100 | 100 | 100 | — | 40 | 95 | 90 | 100 | 100 | 40 |
| 13 | 0.14 | 100 | 98 | 100 | 100 | — | 20 | 100 | 100 | 100 | 100 | 20 |
| 14 | 0.070 | 70 | 100 | 100 | 100 | — | 50 | 100 | 100 | 80 | 100 | 90 |
| 15 | 0.035 | 100 | 100 | 70 | 100 | — | 40 | 100 | 100 | 90 | 100 | 55 |
| 16 | 0.14 | 95 | 95 | 100 | 100 | — | 45 | 100 | 100 | 80 | 100 | 20 |
| 17 | 0.56 | 55 | 100 | 100 | 100 | — | 45 | 100 | 100 | 95 | 100 | 20 |
| 18 | 0.14 | 100 | 100 | 100 | 100 | — | 50 | 100 | 78 | 100 | 100 | 20 |
| 19 | 0.14 | 100 | 100 | 100 | 100 | — | 20 | 100 | 100 | 100 | 100 | 70 |
| 20 | 0.070 | 100 | 100 | 70 | 100 | — | 30 | 95 | 100 | 95 | 100 | 65 |
| 21 | 0.14 | 75 | 100 | 100 | 100 | — | 20 | 100 | 100 | 100 | 100 | 20 |
| 22 | 0.28 | 100 | 100 | 50 | 100 | — | 40 | 100 | 100 | 100 | 100 | 78 |
| 23 | 0.14 | 100 | 100 | 100 | 100 | — | 78 | 100 | 100 | 100 | 100 | 95 |
| 24 | 0.14 | 100 | 100 | 100 | 100 | — | 30 | 100 | 100 | 45 | 100 | 35 |
| 25 | 0.28 | 90 | 100 | 100 | 100 | — | 20 | 80 | 100 | 80 | 100 | 78 |
| 26 | 0.28 | 100 | 100 | 100 | 100 | — | 20 | 20 | 100 | 80 | 100 | 70 |
| 27 | 0.28 | 100 | 100 | 70 | 100 | — | 45 | 100 | 100 | 100 | 100 | 65 |
| 28 | 0.14 | 100 | 100 | 100 | 100 | 100 | 45 | 100 | 90 | 80 | 100 | 50 |
| 29 | 0.070 | 100 | 100 | 100 | 85 | 45 | 45 | 100 | 75 | 45 | 100 | 45 |
| 30 | 0.14 | 100 | 100 | 100 | 100 | 90 | 95 | 100 | 100 | 100 | 100 | 100 |
| 31 | 1.12 | 50 | 100 | 100 | 70 | 55 | 0 | 85 | 60 | 40 | 55 | 0 |
| 32 | 0.035 | 40 | 100 | 90 | 100 | 50 | 20 | 10 | 100 | 99 | 90 | 50 |
| 33 | 0.070 | 100 | 100 | 90 | 90 | 20 | 90 | 85 | 100 | 95 | 85 | 98 |
| 34 | 0.035 | 95 | 100 | 100 | 100 | 60 | 50 | 100 | 100 | 100 | 95 | 100 |
| 35 | 0.14 | 100 | 100 | 100 | 80 | 65 | 90 | 100 | 100 | 100 | 100 | 100 |
| 36 | 0.14 | 100 | 100 | 100 | 100 | 40 | 20 | 50 | 95 | 60 | 100 | 80 |
| 37 | 0.070 | 100 | 100 | 100 | 100 | 70 | 40 | 80 | 100 | 100 | 100 | 45 |
| 38 | 0.070 | 45 | 100 | 100 | 100 | 30 | 20 | 100 | 95 | 95 | 100 | 20 |
| 39 | 0.070 | 100 | 100 | 70 | 100 | 40 | 0 | 90 | 100 | 65 | 100 | 0 |
| 40 | 0.035 | 100 | 100 | 95 | 95 | 60 | 0 | 70 | 90 | 20 | 100 | 20 |
| 41 | 0.14 | 95 | 100 | 100 | 100 | 78 | 65 | 100 | 100 | 65 | 100 | 78 |
| 42 | 0.14 | 100 | 100 | 65 | 30 | 60 | 20 | 100 | 100 | 50 | 100 | 20 |

TABLE 3-continued

PREEMERGENCE HERBICIDAL ACTIVITY

| Cpd. No. | Rate, Kg/Ha | BWCKB | BWLMQ | BWPIG | BWVEL | BWWPT | GWBLG | GWBRN | GWCRB | GWGFT | GWROX | GWWOT |
|---|---|---|---|---|---|---|---|---|---|---|---|---|
| 43 | 0.14 | 100 | 100 | 100 | 20 | 50 | 20 | 90 | 100 | 90 | 80 | 50 |
| 44 | 0.28 | 60 | 100 | 100 | 30 | 0 | 100 | 100 | 40 | 100 | 30 |
| 45 | 0.28 | 50 | 100 | 100 | 100 | 0 | 0 | 100 | 100 | 40 | 70 | 20 |
| 46 | 0.28 | 100 | 100 | 100 | 70 | 30 | 20 | 50 | 100 | 30 | 100 | 80 |
| 47 | 0.28 | 100 | 100 | 100 | 40 | 30 | 90 | 55 | 100 | 20 | 100 | 70 |
| 48 | 0.28 | 100 | 100 | 65 | 65 | 40 | 50 | 80 | 100 | 60 | 100 | 65 |
| 49 | 0.14 | 100 | 100 | 100 | 5 | 30 | 20 | 100 | 100 | 60 | 100 | 20 |
| 51 | 0.14 | 55 | 100 | 100 | 100 | 55 | 0 | 100 | 100 | 90 | 100 | 0 |
| 52 | 0.56 | 20 | 95 | 100 | 100 | 70 | 0 | 100 | 100 | 80 | 100 | 0 |
| 53 | 0.56 | 100 | 100 | 100 | 100 | 60 | 50 | 100 | 100 | 70 | 100 | 80 |
| 54 | 0.28 | 90 | 100 | 100 | 100 | 30 | 20 | 100 | 100 | 70 | 50 | 20 |
| 55 | 0.28 | 0 | 100 | 100 | 70 | 40 | 0 | 78 | 100 | 55 | 100 | 20 |
| 56 | 0.56 | 100 | 100 | 100 | 100 | 45 | 45 | 20 | 100 | 100 | 100 | 0 |
| 57 | 0.14 | 100 | 95 | 100 | 100 | 60 | 0 | 90 | 100 | 90 | 95 | 20 |
| 58 | 0.14 | 100 | 100 | 100 | 100 | 30 | 20 | 100 | 70 | 60 | 100 | 20 |
| 59 | 0.28 | 70 | 100 | 100 | 100 | 70 | 45 | 100 | 100 | 80 | 100 | 30 |
| 60 | 0.56 | 100 | 90 | 100 | 100 | 20 | 50 | 50 | 100 | 20 | 100 | 0 |
| 61 | 0.28 | 100 | 95 | 100 | 100 | 30 | 40 | 30 | 100 | 50 | 100 | 20 |
| 62 | 0.56 | 100 | 95 | 80 | 78 | 5 | 55 | 20 | 30 | 20 | 100 | 20 |
| 63 | 0.14 | 100 | 95 | 95 | 100 | 55 | 30 | 100 | 100 | 80 | 100 | 0 |
| 69 | 0.28 | 80 | 100 | 100 | 90 | 30 | 50 | 100 | 100 | 100 | 45 | 0 |
| 70 | 0.28 | 100 | 100 | 75 | 99 | 40 | 0 | 99 | 100 | 70 | 30 | 0 |
| 72 | 0.14 | 100 | 100 | 100 | 100 | 50 | 10 | 100 | 100 | 100 | 100 | 0 |
| 74 | 0.14 | 100 | 100 | 100 | 100 | 75 | 0 | 65 | 98 | 60 | 70 | 0 |
| 75 | 0.28 | 100 | 100 | 100 | 60 | 0 | 5 | 60 | — | 99 | 95 | 70 |
| 76 | 0.28 | 100 | 100 | 100 | 100 | 80 | 0 | 100 | 100 | 100 | 100 | 65 |
| 77 | 0.070 | 100 | 100 | 100 | 100 | 60 | 45 | 75 | 100 | 100 | 100 | 70 |
| 78 | 0.14 | 98 | 100 | 100 | 100 | 60 | 95 | 80 | 100 | 100 | 100 | 85 |
| 79 | 0.14 | 95 | 100 | 100 | 80 | 70 | 0 | 65 | 100 | 100 | 80 | 60 |
| 80 | 0.28 | 80 | 100 | 100 | 85 | 75 | 20 | 65 | 100 | 100 | 100 | — |
| 81 | 0.56 | 50 | 100 | 100 | 100 | 10 | 10 | 10 | 100 | 20 | 30 | 50 |
| 82 | 0.14 | 90 | 100 | 100 | 100 | 0 | 0 | 0 | 100 | 90 | 70 | 20 |
| 83 | 0.070 | 100 | 100 | 100 | 100 | 50 | 25 | 100 | 100 | 100 | 85 | 60 |
| 84 | 0.14 | 100 | 100 | 100 | 100 | 30 | 65 | 85 | 100 | 100 | 100 | 70 |
| 85 | 0.14 | 100 | 100 | 100 | 90 | 30 | 80 | 100 | 100 | 100 | 100 | 80 |
| 87 | 0.56 | 100 | 100 | 70 | 100 | 20 | 100 | 30 | 100 | 40 | 65 | 100 |
| 88 | 0.14 | 60 | 100 | 100 | 100 | 40 | 60 | 100 | 100 | 80 | 100 | 100 |
| 89 | 0.070 | 55 | 100 | 100 | 20 | 30 | 40 | 78 | 100 | 75 | 100 | 55 |
| 91 | 0.28 | 45 | 100 | 30 | 100 | 20 | 55 | 100 | 60 | 30 | 80 | 80 |
| 93 | 0.28 | 70 | 100 | 55 | 100 | 45 | 55 | 100 | 100 | 90 | 100 | 55 |
| 96 | 0.070 | 70 | 100 | 100 | 95 | 55 | 20 | 100 | 100 | 100 | 100 | 45 |

BWCKB = cocklebur (*Xanthium strumarium*)
BWLMQ = lambsquarters (*Chenopodium album*)
BWMGL = morningglory (*Ipomoea hederacea*)
BWPIG = pigweed (*Amaranthus retroflexus*)
BWVEL = velvetleaf (*Abutilion theophrasti*)
BWWPT = wild poinsettia (*Euphorbia heterophylla*)
GWBLG = blackgrass (*Alopecurus myosuroides*)
GWBRN = barnyardgrass (*Echinochloa crus-galli*)
GBCRB = crabgrass (*Digitaria sanguinalis*)
GWGFT = giant foxtail (*Setaria faberi*)
GWROX = Rox orange sorghum (*Sorghum bicolor*)
GWWOT = wild oats (*Avena fatua*)

What is claimed is:

1. A benzoic acid compound of the formula:

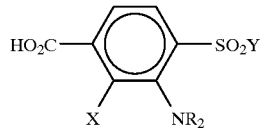

wherein

X represents F, Cl, Br, $C_1$–$C_4$ alkyl, $OCH_3$, $OC_2H_5$, $Ch_2OCH_3$, or $CH(CH_3)OCH_3$;

Y represents $CH_3$, $C_2H_5$, or $CH(CH_3)_2$; and each R independently represents H or $C_1$–$C_4$ alkyl, $C_3$–$C_4$ alkenyl, or $C_3$–$C_4$ alkynyl (each optionally possessing up to two substituents selected from Cl, Br, CN, $C_1$–$C_4$ alkoxy, and $C_1$–$C_3$ fluoroalkoxy and up to three F substituents) or benzyl (optionally possessing up to three ring substituents selected from F, Cl, Br, CN, $CF_3$, $NO_2$, $CH_3$, $C_2H_5$, $OCH_3$, and $OC_2H_5$); with the proviso that both of R do not represent H; or $NR_2$ represents a 4- to 7-membered aliphatic nitrogen heterocyclic substituent optionally possessing O as a second ring heteroatom, optionally possessing one double bond, and optionally possessing up to three substituents selected from F, Cl, Br, CN, $C_1$–$C_4$ alkyl, $C_1$–$C_3$ fluoroalkyl, $C_1$–$C_4$ alkoxy, $C_1$–$C_3$ fluoroalkoxy, $C_1$–$C_3$ alkoxymethyl, and phenyl (optionally possessing up to three ring substituents selected from F, Cl, Br, CN, $CF_3$, $NO_2$, $CH_3$, $C_2H_5$, $OCH_3$, and $OC_2H_5$); or $NR_2$ represents a pyrrol-1-yl or pyrazol-1-yl moiety optionally possessing up to two substituents selected from F, Cl, Br, I, CN, $CF_3$, $C_1$–$C_3$ alkyl, and $C_1$–$C_3$ alkoxy.

2. A compound according to claim 1 wherein Y represents methyl.

3. A compound according to claim 1 wherein X represents chloro or methyl.

4. A compound according to claim 1 wherein each R independently represents methyl, ethyl, or 2-methoxyethyl or wherein one of R represents hydrogen and the other represents methyl, ethyl, or 2-methoxyethyl.

5. A compound according to claim 1 wherein $NR_2$ represents a 5- or 6-membered aliphatic nitrogen heterocyclic substituent optionally having one ring oxygen heteroatom and optionally substituted by one or two methyl or methoxy substituents.

6. A compound according to claim 5 wherein $NR_2$ represents morpholin-4-yl.

* * * * *